US007575934B2

(12) United States Patent
Atwood

(10) Patent No.: US 7,575,934 B2
(45) Date of Patent: Aug. 18, 2009

(54) ORIENTED MAGNETIC PARTICLE-FLUORESCENCE DETECTABLE MOIETY COMPOSITIONS AND METHODS OF MAKING AND USING THE SAME

(75) Inventor: Christopher G. Atwood, San Diego, CA (US)

(73) Assignee: Nativis, Inc., La Jolla, CA (US)

( * ) Notice: Subject to any disclaimer, the term of this patent is extended or adjusted under 35 U.S.C. 154(b) by 274 days.

(21) Appl. No.: 11/825,249

(22) Filed: Jul. 3, 2007

(65) Prior Publication Data

US 2008/0011977 A1    Jan. 17, 2008

Related U.S. Application Data

(60) Provisional application No. 60/819,025, filed on Jul. 7, 2006.

(51) Int. Cl.
  *G01N 33/543* (2006.01)
(52) U.S. Cl. .................. 436/165; 436/172
(58) Field of Classification Search ........... None
  See application file for complete search history.

(56) References Cited

OTHER PUBLICATIONS

Melle et al., "Structure and dynamics of magnetorheological fluids in rotating magnetic fields" The American Physical Society: Physical Review E, vol. 61, No. 4, pp. 4111-4117 (Apr. 2000).*
Chemla, Y. et al., *PNAS*, 97:14268-72 (2000).
Crut, A. et al., *Nucleic Acids Res.*, 33(11):e98, pp. 1-9 (2005).
Dubertret, B. et al., Science, 298:1759-62 (2002).
Gao, X. et al., *Current Opinion in Biotechnology*, 16:63-72 (2005).
Grabarek, Z. and Gergely, *J. Anal. Biochem.*, 185:131-35 (1990).
Haller et al., *IEEE Transactions on Applied Superconductivity*, 11:1371-74 (2001).
Han et al., *Nature Biotechnology*, 19:631-35 (2001).
Hendrickson, *BioTechniques*, 3:198-207 (1985).
Magana, D. J.,Am. Chem. Soc., 2006: ASAP Article 10.1021/ja055785tS0002-7863(05)05785-9, Web Release Date: Feb. 10, 2006.
Moini, H. et al.,*Methods Enzymol.*, 335:333-37 (2001).
Mulvaney, S. et al., *BioTechniques*, 36:602-609 (2004).
Nuzzo, R., *J. Am. Chem. Soc.*, 105:4481-83 (1983).
Olivos, H. et al., *Chem. BioChem.*, 4:1242-45 (2003).
Staros, J. et al., *Anal. Biochem.*, 156:220-22 (1986).
Wikswo, J. et al., *Science*, 208:53-55 (1980).
Yi, D. et al., *J. Am. Chem. Soc.*, 127:4990-91 (2005).

* cited by examiner

*Primary Examiner*—Yelena G Gakh
*Assistant Examiner*—Dirk Bass
(74) *Attorney, Agent, or Firm*—King & Spalding LLP

(57) ABSTRACT

Compositions and methods relating to magnetic particles comprising one or more fluorescence detectable moieties positioned asymmetrically with respect to the magnetic pole regions of the particles are described. The compositions are useful for detecting analytes.

10 Claims, 18 Drawing Sheets

Rotation and Occultation

Rotation time = 2.185 ms

Rotation time = 2.059 ms

Magnetic Particles
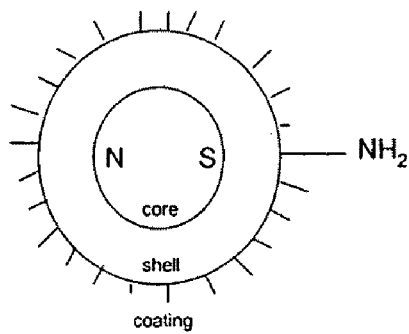
Core is ~ 500 nm diameter
(Fe, γFe$_2$O$_3$, ferrites, etc.)
magnetic moment
$1.25 \times 10^{-14}$ A · m$^2$
Shell is ~ 1000 nm diameter
(SiO$_2$)
Coating is amine, etc.
Fig. 1
Particle Size
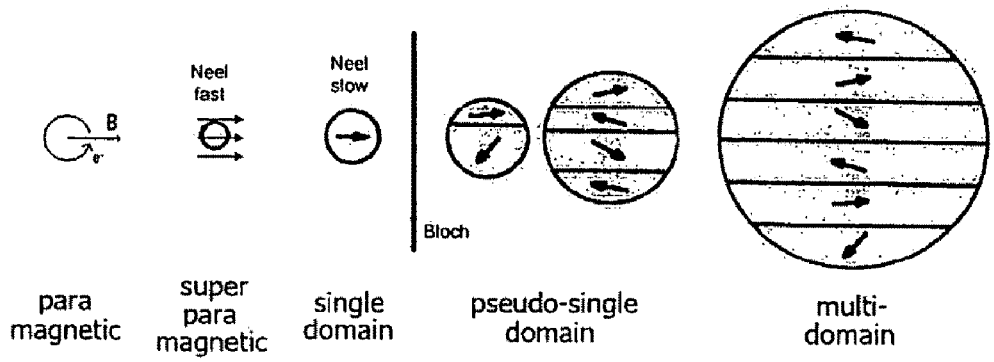
para magnetic | super para magnetic | single domain | pseudo-single domain | multi-domain
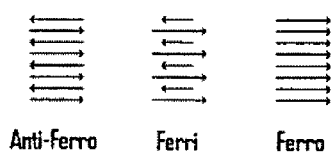
Anti-Ferro | Ferri | Ferro
Fig. 2

For γ-Fe₂O₃ (maghemite):

Bloch (domain) limit is 500 nm

Néel Relaxation time $\tau_N = \tau_0 \exp(KV/k_BT)$ $\tau_0$ = Larmor period = $10^{-9}$ s
K is crystalline anisotropy constant = 5000 J m⁻³
   (depends on composition, shape and surface)
V is particle volume
$k_B$ is Boltzman constant = $1.38 \times 10^{-23}$ J K⁻¹
T is absolute temperature = 293 K 500 nm → $5 \times 10^{-19}$ m³ → $10^{-9}$ s exp(618000) → "infinite" s

Fig. 3

Particle Chaining

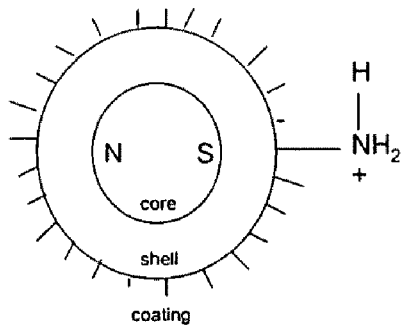

*Core* is a bar magnet that tends to cause chaining

*Shell* has significant thickness to discourage chaining

*Coating* is charged, which electrostatically discourages chaining

Fig. 4

Quantum Dots

Core is ~ 10 nm diameter
(CdS, CdSe, or CdTe)
highly fluorescent
broad absorption
narrow emission (30 nm)
size determines λ

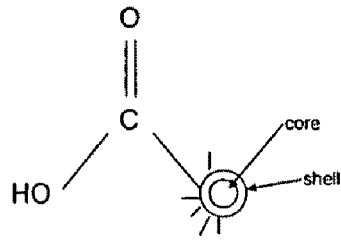

Shell is ~ 20 nm diameter
(ZnS)

Coating is carboxylic acid, etc.

Fig. 5

Quantum Dot
Absorbance
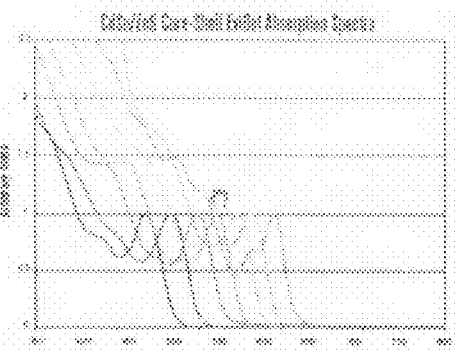
Emission
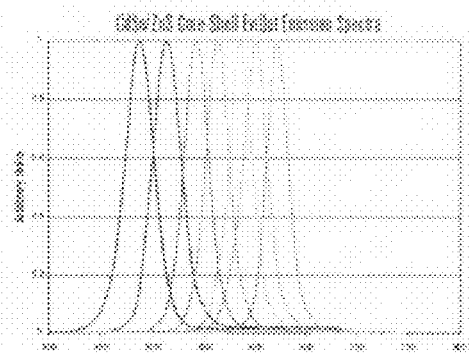
Fig. 6A                    Fig. 6B
Oriented Linking
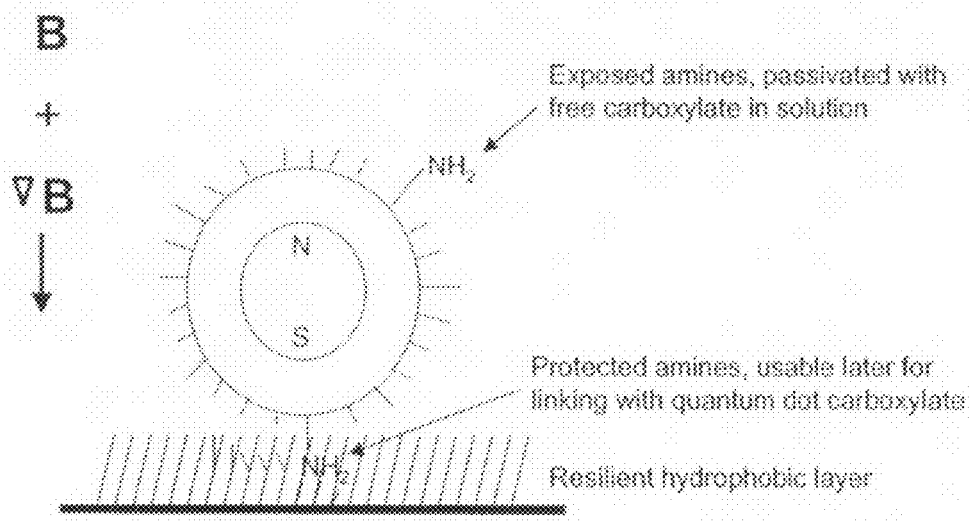
Fig. 7

Hydrophobic Monolayer

Resilience Adjustment

C12 self assembled monolayer

Rigid Crystal

Mixed C12 and C18 self assembled monolayer

Resilient Mixture

C18 self assembled monolayer

Rigid Crystal

Magnetic Particles + Quantum Dots

Link NH₂ and COOH using EDC and Sulfo-NHS in a *specific* orientation

Linking Reaction

Rotational Drag
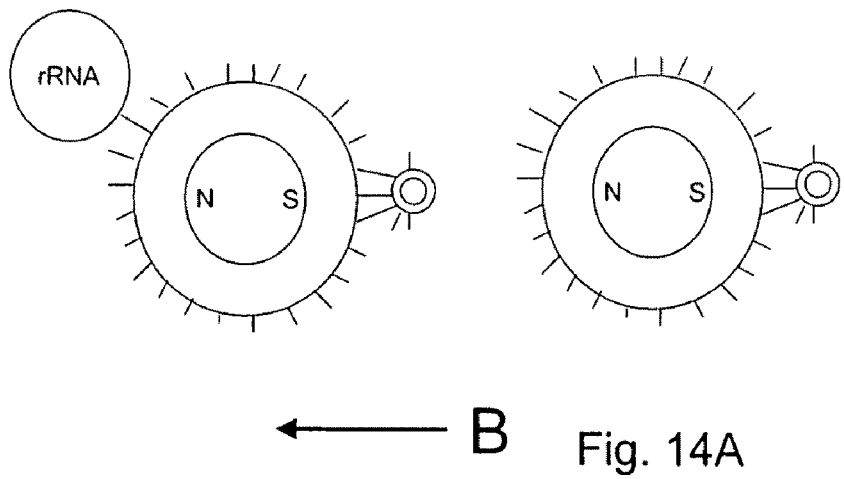
← B    Fig. 14A
Rotational Drag
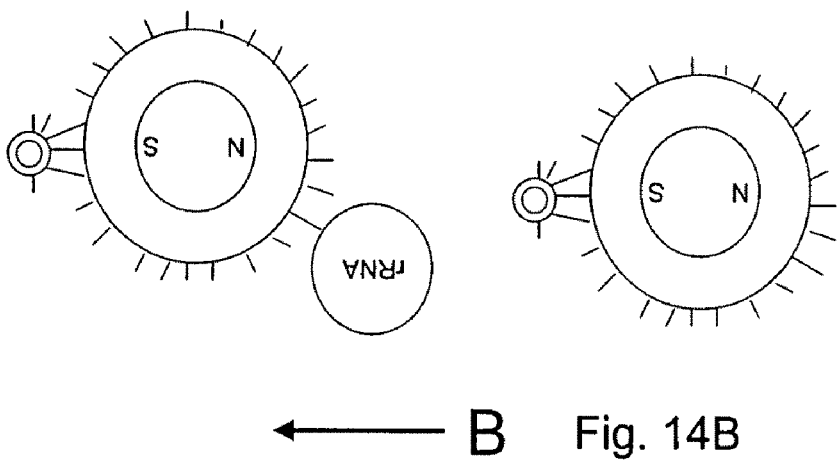
← B    Fig. 14B

Rotation and Occultation
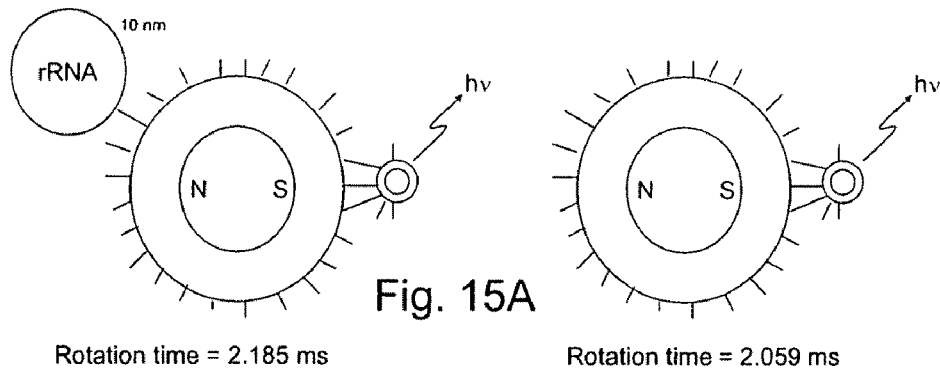
Rotation time = 2.185 ms  Rotation time = 2.059 ms
Fig. 15A
Fig. 15B
Solenoid
1.8 mTesla
309 Hz
Fluorescence Emission
ΔPhase = 14 deg
Migration
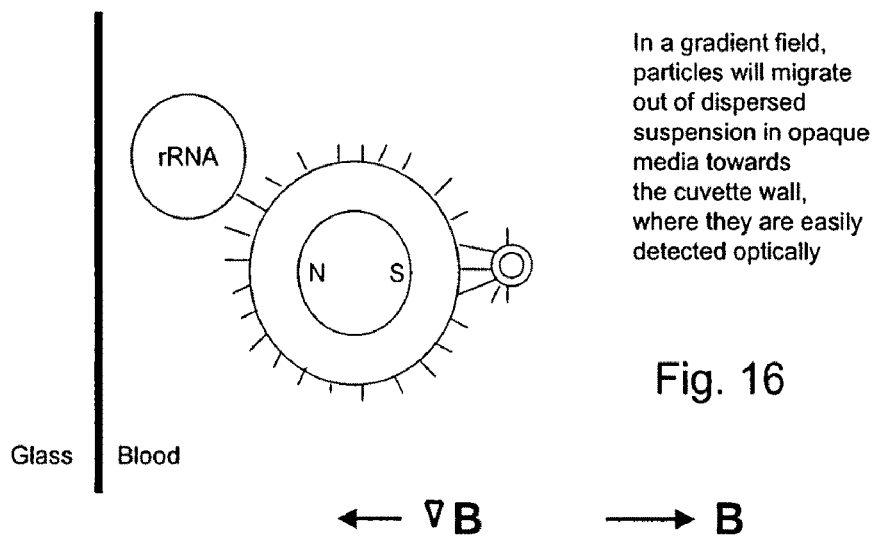
In a gradient field, particles will migrate out of dispersed suspension in opaque media towards the cuvette wall, where they are easily detected optically
Fig. 16
Glass | Blood
← ∇B   → B

Evanescent Excitation

← ∇B

Enhancement of occultation

Solenoid

When current through a solenoid is oscillated:

The magnetic field B changes direction, causing particle rotation

The magnetic force due to ∇B does *not* change direction, causing consistent migration

US 7,575,934 B2

ORIENTED MAGNETIC PARTICLE-FLUORESCENCE DETECTABLE MOIETY COMPOSITIONS AND METHODS OF MAKING AND USING THE SAME

RELATED APPLICATIONS

The present application claims priority to U.S. Provisional Application Ser. No. 60/819,025, filed on Jul. 7, 2006, which is hereby incorporated by reference.

TECHNICAL FIELD

The compositions and methods relate to magnetic particles having one or more fluorescence detectable moieties positioned asymmetrically with respect to the magnetic pole regions of the particle for using in detecting and characterizing an analyte.

BACKGROUND

Single domain and multidomain derivatized magnetic particles have been used for ligand-receptor binding measurements in a technique called "MAgnetic Relaxation ImmunoAssay" (MARIA). Ligand-receptor binding determination using MARIA has been described by Eberbeck, D. et al. *J. Magnet. Magn. Mat.*, 2005, 289:435-38; Haller, A. et al. *IEEE Transactions on Applied Superconductivity*, 2001, 11:1371-74; Ludwig, F. et al. *J. Magnet. Magn. Mat.*, 2005 293:690-95; Matz, H. *Applied Superconductivity*, 1999, 6:577-83; Kötitz, R. *J. App. Phys.*, 1997, 81:4317; Kotitz, R. et al. *J. of Magnet. Magn. Mat.*, 1999, 194:62-68; Weitschies, W. *Pharm. Pharmacol. Lett.*, 1997, 7:1-7; Chemla, Y. et al. *PNAS*, 2000, 97:14268-72.

MARIA involves suspending ligand-derivatized particles in solvated receptors, applying a momentary strong magnetic field to align and magnetize the particles, and then turning off the field and measuring the remnant sample magnetization with a SQUID. Non-binding particles will rapidly randomize their orientations due to Brownian motion, resulting in a rapid decay of the SQUID signal. Binding particles will rotate slower due to frictional and momentum effects, causing the SQUID signal to decay more slowly. This technique can be used in a complex biological matrix without purification steps, but only one binding experiment can be performed per sample.

Derivatized quantum dots have also been used for binding measurements (Ravindran, S. et al. *Nanotechnology* 2005, 1; Olivos, H. et al. *Chem. BioChem.* 2003, 4:1242-45). Because of the narrow emission bands, combinations of dots (i.e., multiplexing) is possible. Binding measurements have been performed using gel electrophoresis and chromatographic methods (Moini, H. et al. *Methods Enzymol.* 2001, 335:333-7; Hendrickson, W. *BioTechniques* 1985, 3:198-207; Afjehi-Sadat, L. et al. *Current Proteomics* 2004, 1:297-313), which exploit the differing migration speeds of the components in a mixture to effect a physical separation of the components.

Magnetic particles and quantum dots have heretofore been combined (Selvan, S. et al. *Advanced Materials*, in press; Yi, D. *J. Am. Chem. Soc.*, 2005, 127:4990-91; Mulvaney, S. *BioTechniques*, 2004, 36:602-09) but not in an asymmetric configuration with respect to the magnetic pole, which permits novel applications to be described.

REFERENCES

Each of the following reference, as well as additional references cited herein, are incorporated by reference in their entirety.

Afjehi-Sadat, L. et al. *Current Proteomics* 2004, 1:297-313;
Afremov, L. and Panov, A. *Physics of Metals and Metallography*, 1998, 86:269-275;
Chemla, Y. et al. *PNAS*, 2000, 97:14268-72;
Crut, A. et al. *Nucleic Acids Res.*, 2005, 33:e98;
Ditsch, A. et al. *Magnetic Nanofluids for Chemical and Biological Processing*, Dept. of Chemical Engineering, Massachusetts Institute of Technology;
Dubertret, B. et al. *Science*, 2002, 298:1759-62;
Eberbeck, D. et al. *J. Magnet. Magn. Mat.*, 2005, 289:435-38;
Gao, X. et al. *Current Opinion in Biotechnology*, 2005, 16:63-72;
Grabarek, Z. and Gergely, J. *Anal. Biochem.*, 1990, 185:131-35;
Haller, A. et al. *IEEE Transactions on Applied Superconductivity*, 2001, 11:1371-74;
Han, M. et al. *Nature Biotechnology*, 2001, 19:631-35
Hendrickson, W. *BioTechniques*, 1985, 3:198-207;
Hergt, R. et al. *IEEE Transactions on Magnetics*, 1998: 34:3745-54);
Horak, D. et al. *Macromol. Mater. Eng.*, 2004, 289: 341-348;
Hunt, C. et al. *Rock Physics and Phase Relations: A Handbook of Physical Constants*, American Geophysical Union, 1995, pp 189-204;
Jeong, J. et al. *Journal of Magnetism and Magnetic Materials*, 2005, 286:5-9);
Kotitz, R. et al. *J. of Magnet. Magn. Mat.*, 1999, 194:62-68;
Kötitz, R. *J. App. Phys.*, 1997, 81:4317;
Lopez-Diaz, L. et al. *Phys. Rev. B*, 2002, 65:224406;
Ludwig, F. et al. *J. Magnet. Magn. Mat.*, 2005 293:690-95;
Matz, H. *Applied Superconductivity*, 1999, 6:577-83;
Magana, D. *J. Am. Chem. Soc.*, 2006: ASAP Article 10.1021/ja055785tS0002-7863(05)05785-9, Web Release Date: Feb. 10, 2006;
Martinez, B. et al. *Phys. Rev. Lett.*, 1998, 80:181-84;
Martinicka, F. and Simacek, I. *Measurement Science Review*, 2003, 3:91-94;
Moini, H. et al. *Methods Enzymol.*, 2001, 335:333-37;
Mulvaney, S. et al. *BioTechniques*, 2004, 36:602-609;
Murray et al. *Nature*, 2003, 25;
Néel, L. *Ann. Geophys.*, 1949, 5:99-136;
Néel, L. *J. Physique Rad.*, 1954, 15:225-39;
Nuzzo, R. *J. Am. Chem. Soc.*, 1983, 105:4481-83;
Olivos, H. et al. *Chem. BioChem.*, 2003, 4:1242-45;
Pouya, S. et al. *Experiments in Fluids*, 2005, 39:784-86;
Ravindran, S. et al. *Nanotechnology*, 2005, 1;
Reitz, J. et al. *Foundations of Electromagnetic Theory*, Third Edition, Addison-Wesley Publishing Co., 1980, pp. 165;
Rosensweig, R. *Ferrohydrodynamics*, Cambridge University Press, 1985;
Scherer, C. and Figueiredo, A. Braz. *J. Phys.*, 2005: 35:3a;
Selvan, S. et al. *Advanced Materials*, in press;
Staros, J. et al. *Anal. Biochem.*, 1986, 156:220-22;
Weitschies, W. *Pharm. Pharmacol. Lett.*, 1997, 7:1-7;
Wikswo, J. et al. *Science*, 1980, 208:53-55;

Winter, J. et al. *Adv. Mater.*, 2001, 13:1673-77; and Yi, D. et al. *J. Am. Chem. Soc.*, 2005, 127:4990-91.

SUMMARY

In one aspect, a fluorescence-detectable composition is provided, comprising:

a magnetic particle having stable north and south-pole magnetic regions, and one or more fluorescent moieties attached to the magnetic particle and having an asymmetric spatial localization with respect to said north- and south-pole regions. In some embodiments, the fluorescent moieties are localized adjacent one of the two poles of the magnetic particles. In some embodiments, the fluorescent moieties include a defined emission spectrum in the visible light range.

In some embodiments, the composition further includes, covalently linked to the surface of the magnetic particle, anti-ligand molecules capable of binding specifically with ligand molecules to which the composition is exposed in solution. In particular embodiments, the anti-ligand and ligand molecules form pairs of molecules selected from the group consisting of (i) antigen-antibody molecules, (ii) ligand-receptor molecules, and complementary nucleic acid molecules.

In some embodiments, the fluorescent moieties include a first group of one or more fluorescent moieties localized asymmetrically at one region of the magnetic particle and having a first emission color, and a second group of one or more fluorescent moieties localized asymmetrically at a second region of the magnetic particle and having a second emission color.

In particular embodiments, the composition includes three groups of one or more fluorescent moieties localized asymmetrically at each of three regions of the magnetic particle and having a first, second, and third emission colors, respectively, with red, blue, and green spectral emission wavelengths (i.e., emission colors), respectively.

In some embodiments, the composition further includes a non-magnetic particle attached to the magnetic particle to reduce magnetic interaction between the compositions.

In some embodiments, the magnetic particle is formed of a single-domain inner ferromagnetic or ferrimagnetic core covered by a non-magnetic shell whose surface contains chemical groups through which the fluorescent moieties are covalently attached to magnetic particles.

In some embodiments, the magnetic particle is formed by precipitating a magnetically active material within a polymer sphere while a strong external magnetic field is applied, causing the precipitate to have a net non-zero magnetic field and the polymer sphere to have a distinct North and South pole.

In some embodiments, the one or more fluorescent moieties include one or more quantum-dot particles. In particular embodiments, the quantum-dot particle is formed of a fluorescent inorganic salt core covered by a non-fluorescent shell whose surface contains chemical groups through which the magnetic particle is covalently attached to quantum-dot particles.

In particular embodiments, the core of the quantum-dot particles is a cadmium salt selected from CdS, CdSe, and CdTe, and the shell is formed of ZnS. In still more particular embodiments, the composition further includes a second magnetic particle covalently bound to a quantum-dot particle, where the internal magnetic fields of the two magnetic particles are at least partially aligned. In some embodiments, the fluorescent moieties are fluorescent molecules. In some embodiments, the fluorescent moieties are attached physically to the magnetic particles. In particular embodiments, the fluorescent moieties are attached covalently to the magnetic particles.

In another aspect, a method of forming the above composition is provided, comprising:

employing a magnetic field to orient coated magnetic particles in an environment in which a portion of each particle surface is exposed to a selected chemical-treatment environment and the remainder portion is shielded from such environment, where each such portion has a defined orientation with respect to magnetic north-pole and magnetic south-pole regions of the particle, treating the oriented particles with a chemical treatment effective to selectively attach or create desired chemical groups to the exposed portion of each particle, and coupling one or more fluorescent moieties to the magnetic particles through such chemical groups.

In some embodiments, the environment in which a portion of each particle surface is exposed to a selected chemical-treatment environment and the remainder portion is shielded from such environment includes a surface having formed thereon, a monolayer composed of a close-packed array of hydrocarbon chains.

In particular embodiments, the environment in which a portion of each particle surface is exposed to a selected chemical-treatment environment and the remainder portion is shielded from such environment includes a polymer having one of (i) a deformable surface, an (ii) an array of pockets in which a magnetic particle can be cradled, and (iii) a coating of polymer chains.

In some embodiments, the particles are uniformly coated with a light-sensitive protecting agent linked to chemically active groups, and said treating includes exposing said particles, when oriented in a magnetic field, to a coherent light beam directed at the one side of the particles only.

In some embodiments, the particles are oriented at the interface between two immiscible liquids, and said treating includes treating includes exposing the particles to a chemical reagents contained predominantly in one of the two liquids only.

In some embodiments, the environment is a polymer sheet comprising fluorescent moieties and the oriented particles are heated to coat a portion of the particles contacting the polymer sheet with fluorescent moieties. In some embodiments, the environment is a polymer sheet having pockets comprising fluorescent moieties and the oriented particles are heated to coat a portion of the particles contacting the fluorescent moieties in the pockets.

In some embodiments, the environment is a polymer sheet comprising fluorescent moieties and covering the oriented particles, and the oriented particles are heated to coat a portion of the particles contacting the fluorescent moieties.

In a related aspect, a method of detecting the presence of a ligand analyte is provided, comprising (a) exposing the analyte in solution to a fluorescence-detectable composition comprising (i) a magnetic particle having stable north and south-pole magnetic regions, (ii) one or more fluorescent moieties covalently linked to the magnetic particle and having an asymmetric spatial localization with respect to said north- and south-pole regions, and (iii) anti-ligand molecules covalently linked to the magnetic particle, (b) by said exposing binding the ligand analyte to the surface of said magnetic particle, thereby to increase the rotational drag of the composition when placed in an alternating or rotating electromagnetic field, (c) irradiating the composition with a fluorescence-excitation light beam, while rotating the composition in an alternating or rotating electromagnetic field, and (d) determining, from a measured phase lag of fluorescence emission from the composition, relative to the composition prior to ligand binding, the presence and/or amount of ligand bound to the analyte.

In some embodiments, the one or more fluorescent moieties include one or more quantum-dot particles, the sample and composition are placed in a transparent detection vessel, and which further includes placing the composition in a magnetic force effective to draw the composition adjacent a wall of the vessel, and said irradiating and measuring is carried out at said vessel wall.

In some embodiments, the one or more fluorescent moieties include one or more quantum-dot particles, and the vessel is a glass or quartz cuvette having a wall that supports total internal reflectance of the fluorescence excitation beam, wherein the composition is irradiated by evanescent fluorescence from the cuvette wall.

In particular embodiments, the magnetic field and magnetic force are supplied by a solenoid supplied by an alternating electric current. In particlular embodiments, the particles are placed in the rotating electromagnetic field prior to addition of the analyte.

In some embodiments, the one or more fluorescent moieties include one or more quantum-dot particles suspended in micelles or a weak or dilute gelling agent, thus to minimize linear movement yet allow rotational movement during said irradiating and rotating step.

In some embodiments, the one or more fluorescent moieties include one or more quantum-dot particles, and said rotating step is carried out by (i) rotating the composition quickly to 90 degrees, and (ii) releasing the magnetic force on the composition momentarily, thus to cause identical poles to be opposed in a repellent orientation and thus force magnetic particles in the composition apart.

In one example, the methods are for use in detecting one or more of each of a plurality of analytes, the composition to which the analytes are exposed includes a plurality of compositions, each having a different fluorescence excitation wavelength, and said irradiating includes irradiating the compositions at different selected excitation wavelengths, to interrogate each of the compositions separately.

In another example, the methods are for use measuring the binding affinity and dynamic properties of a ligand analyte to an anti-ligand attached to such a composition, wherein said rotating step is carried out at a plurality of frequencies, to produce a plurality of composition rotational speeds, and the rotational speed effective to release the ligand from the composition is determined. In some embodiments, the particles are placed in the rotating electromagnetic field prior to addition of the analyte.

In a related aspect, a method of detecting the presence of a ligand analyte is provided, comprising (a) providing a fluorescence-detectable composition comprising (i) a magnetic particle having stable north and south-pole magnetic regions, (ii) one or more fluorescent moieties covalently linked to the magnetic particle and having an asymmetric spatial localization with respect to said north- and south-pole regions, and (iii) anti-ligand molecules covalently linked to the magnetic particle, (b) placing said particles in an alternating or rotating electromagnetic field, (c) irradiating the composition with a fluorescence-excitation light beam, while rotating the composition in an alternating or rotating electromagnetic field, (d) exposing the ligand analyte to the surface of said magnetic particle to increase the rotational drag of the composition, and (e) determining, from a measured phase lag of fluorescence emission from the composition, relative to the composition prior to ligand binding, the presence and/or amount of ligand bound to the analyte.

These and other objects and features of the invention will become more fully apparent when the following detailed description of the invention is read in conjunction with the accompanying drawings.

BRIEF DESCRIPTION OF THE DRAWINGS

FIG. 1 shows the basic features of a magnetic particle;

FIG. 2 illustrates magnetic properties of single- and multi-domain ferromagnets;

FIG. 3 shows the calculation for relaxation time in a magnet as a function of domain size;

FIG. 4 illustrates how the shell and coating of a magnetic particle may be designed to minimize the tendency of magnetic particles to form chains;

FIG. 5 shows the basic features of a quantum-dot;

FIGS. 6A and 6B show fluorescence excitation (6A) and fluorescence emission (6B) curves for a series of quantum dots;

FIG. 7 illustrates a step in oriented linking to a magnetic particle;

FIGS. 14A and 14B show the composition of the invention in two rotational states;

FIGS. 15A and 15B illustrate the principle of rotation and occultation employed in a detection method of the invention;

FIG. 16 illustrates a simultaneous magnetic force and alternating field for detecting a composition near the surface of a cuvette;

DETAILED DESCRIPTION

I. Introduction

Figure 8A:
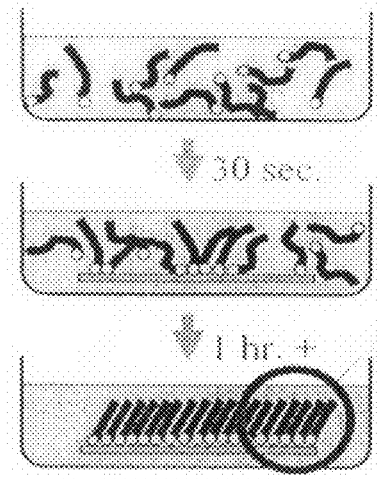
FIGS. 8A and 8B illustrate steps in constructing a hydrocarbon monolayer film for producing oriented linking (8A) and shows the resulting monolayer film (8B)

The present compositions and methods related to magnetic particles having fluorescence detectable moieties positioned asymmetrically with respect to the magnetic pole of the particle. The particle composition may further include assay reagents (i.e., anti-ligands) for binding analytes that encounter by the particles in solution or suspension. The structure of these compositions, methods of preparing the compositions, and methods of using the compositions are to be described.

II. Magnetic Particles

A. General Physical Properties

The manufacture and derivatization of magnetic particles is well known and many reagents are commercially available. Current manufacturers of magnetic particles include but are not limited to BioClone, Inc. (San Diego, Calif., USA), Seradyn (Heidelberg, Germany), Promega (Madison, Wis., USA), Polysciences, Inc. (Warrington, Pa., USA), Chemagen AG (Baesweiler, Germany), Vector Laboratories, Inc. (Burlingame, Calif., USA), and Roche (Basel, Switzerland).

Magnetic cores can be manufactured from Fe, maghemite ($\gamma$-$Fe_2O_3$), and various ferrites from about 50 nm to 500 nm in diameter, enclosed in a silica shell from 500 to 1000 nm diameter, and with a surface chemistry that is customizable for a wide variety of client needs. An exemplary spherical magnetic particle is shown in FIG. 1.

Magnetic particles may be solid particles comprising a single paramagnetic center. Alternatively, magnetic particle suitable may consists of a collection of paramagnetic centers whose orientations spontaneously align ferromagnetically, ferrimagnetically, or anti-ferromagnetically, due to quantum mechanical effects (Scherer and Figueiredo, A. *Braz. J. Phys.* 2005, 35:3a). This spontaneous alignment is called "superparamagnetism." These quantum effects can span for tens, hundreds, or even thousands of centers, depending on the type of material, before being overwhelmed by thermodynamic processes. Such a span creates a magnetic "domain", with a distinct boundary called a "Bloch wall". For maghemite ($\gamma$-$Fe_2O_3$), the domain size is typically 500 nm across (Horak, D. et al. *Macromol. Mater. Eng.* 2004, 289: 341-348), which is also the diameter of the exemplified magnetic particles.

Commercially available functional groups for modifying magnetic particles include amines, DADPA, carboxy, epoxy, aldehyde, hydrazide, IDA, and silicate groups, which are use by the biotechnology community to attach proteins, antibodies, carbohydrates, lectins, nucleic acids, and other biologically relevant molecules.

The magnetic particles used for the experiments described herein are monodomain, meaning that each particle has a distinct North and South pole. Preferred particles are single/mono-domain particles with diameter of about 500 nm, as shown just to the left of the Bloch wall in FIGS. 2 and 3B. It is important that the particles be of uniform magnetic properties, otherwise the rotation rate (vide infra) will not be well-defined, limiting the resolution of the binding measurement. Recent work (Murray et al. *Nature*, 2003, 25) showed that particle sizes can be controlled to within 5% for very small particles. Increased particle uniformity can be achieved, for example, using magnetically-directed chromatography, sedimentation field flow fractionation, or improved manufacturing techniques. Data relating to the uniformity of the exemplary particles was not available.

While the exemplary particles are monodomain, it is expected that multi-domain particles will produce similar results. Magnetic particles can also be formed by precipitating a magnetically active material within a polymer sphere (i.e., a shell for containing the material) while a strong external magnetic field is applied. The resulting precipitate has a net non-zero magnetic field. Such filled polymer spheres can be chemically or physically modification, as described.

Figure 23:
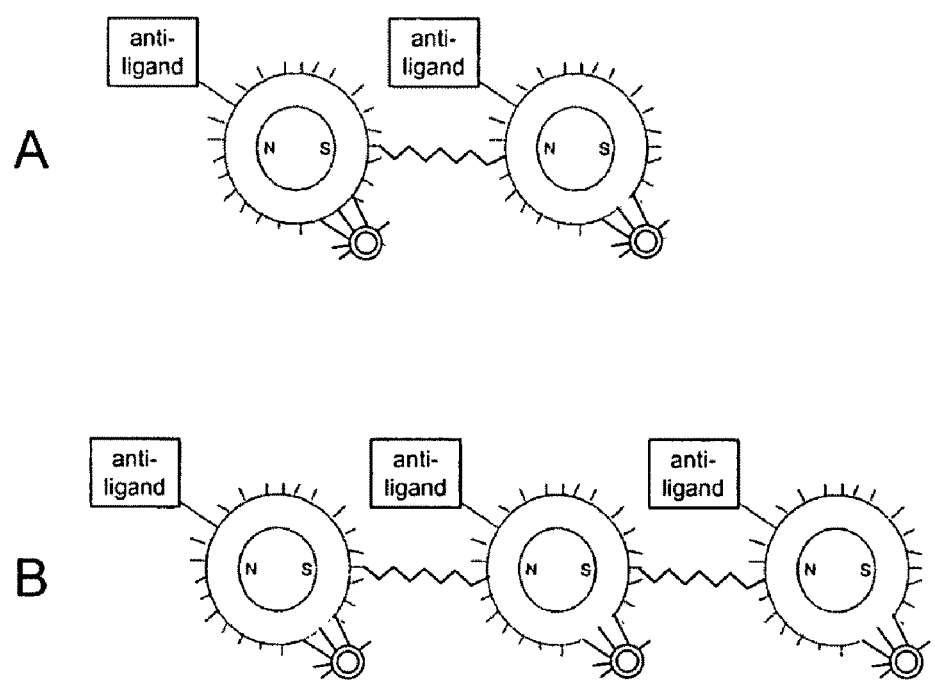
FIGS. 23A and B show two (A) and three (B) magnetic particles linked together to reduce the degrees of freedom of rotation of the particles.

Most embodiments of the invention utilize discrete magnetic particles; however, a plurality of particles can be linked to form chains in which each magnetic particle has a limited degree of freedom to rotate (FIG. 23). This arrangement may is useful where the particles are used in, e.g., a matrix display or screen, as described below. The particles may be linked along any axis, depending on the amount and type of rotation desired.

B. Néel Relaxation Rate

The Néel relaxation rate refers to how quickly a collection of aligned spinning particles (i.e., "spins") will spontaneously re-orient due to thermal agitation above "blocking" temperature. It can be calculated by the following equation (Néel, L. *Ann. Geophys.* 1949, 5:99-136; Néel, L. *J. Physique Rad.* 1954, 15:225-39; Scherer and Figueiredo, A. *Braz. J. Phys.* 2005, 35:3a; Martinicka, F. and Simacek, I. *Measurement Science Review,* 2003, 3:91-94; see FIG. 3A):

$$\tau_N = \tau_0 \exp(KV/k_B T)$$

where $\tau_N$ is the Néel relaxation time, $\tau_0$ is a characteristic Larmor time constant, K is the crystalline anisotropy constant (dependent on composition, shape, and surface characteristics of a particle), V is the volume of the particle, $k_B$ is the Boltzman constant of $1.3807 \times 10^{-23}$ J·$K^{-1}$, and T is the absolute temperature of 293° K.

When $\tau_N$ is less than about several seconds, the particle is called "superparamagnetic" (Lopez-Diaz, L. et al. *Phys. Rev. B,* 2002, 65:224406; Martinez, B. et al. *Phys. Rev. Lett.,* 1998, 80:181-84). Previous work has shown that the Néel relaxation rate exceeds the Brownian rotation rate (vide infra) when the particle size is less than about 12 nm diameter (Ditsch, A. et al. *Magnetic Nanofluids for Chemical and Biological Processing*, Dept. of Chemical Engineering, Massachusetts Institute of Technology).

Larger particles exhibit exponentially slower relaxation rates. For a 500 nm diameter spherical maghemite ($\gamma$-$Fe_2O_3$) particle, $\tau_0$ is approximately $10^{-9}$ s (Rosensweig, R. *Ferrohy-* drodynamics, Cambridge University Press, 1985; Hergt, R. et al. *IEEE Transactions on Magnetics* 1998, 34:3745-54), K is approximately 5000 J·m$^{-3}$, and V is 5×10$^{-19}$ m$^3$. Data relating to physical properties of maghemite are provided in, e.g., Hunt, C. et al. *Rock Physics and Phase Relations: A Handbook of Physical Constants*, American Geophysical Union, 1995, pp 189-204; Afremov, L. and Panov, A. *Physics of Metals and Metallography* 1998, 86:269-275; Horak, D. et al. *Macromol. Mater. Eng.* 2004, 289:341-348; Jeong, J. et al. *Journal of Magnetism and Magnetic Materials*, 2005, 286:5-9). The Néel relaxation time is:

$$\tau_N = 10^{-9} \text{s exp}(61800) \rightarrow \text{"infinite" s}$$

which indicates a sufficient "shelf-life" for the magnetic particles.

III. Derivitization of Magnetic Particles

Derivitaization (or modification) of magnetic particles with fluorescence detectable moieties may be performed using any of several methods. In some embodiments, derivitization is performed by activating and chemically modifying preselected regions of the particles with fluorescence detectable moieties. In other embodiments, derivitization of particles is by physically attaching a fluorescence detectable moiety disposed in a transferable medium, such as a solution, suspension, or polymeric medium. Exemplary methods of derivitization are described, below.

A. Region-specific Chemical Modification of Magnetic Particles

The goal of region-specific chemical modifications is to modify a selected surface region of the particle in relation to the magnetic pole orientation of the particle. Specific regions may be modified directly or entire particles may be modified, followed by the removal of the modification in all but a specific region of the particles. For example, as illustrated in FIG. 7, a magnetic particle coated with amine groups is treated to remove reactive amine groups on the particle except in a small region adjacent the south magnetic pole of the particle.

In the method illustrated in FIG. 7, the particle (typically a large number of particles) is placed in a magnetic field effective to move and orient the particles into an environment in which a preselected surface region of the particle is protected against chemical modification. In the method illustrated in FIG. 7, the protective environment is a resilient hydrophobic layer including a monolayer of oriented hydrocarbon chains (FIGS. 8A and 8B), which may be formed using conventionally methods.

When a particle is placed in a magnetic field of a selected field strength and direction, it will orient as shown in FIG. BA (see also FIGS. 20A-20B) and be drawn against the monolayer surface in the environment, acting to shield the lower surface region of the particle against chemical modification within an aqueous medium in which the particle is suspended or distributed. The extent of shielding (referring to the shielded/protected surface region) will depend on the resilience of the monolayer and the strength of the applied magnetic field.

With the particle so oriented and drawn against the protective monolayer, the particle is then exposed to an aqueous solution effective to passivate or deactivate chemical reactive groups on the exposed portion of the particle. In the example shown in FIGS. 8A and 8B, where the particle is coated by amine groups, the aqueous solution covering the particles may contain amine-reactive groups, such as described below. Amine-reactive groups are effective in replacing the amine groups on the particles with non-reactive groups, for example, by coupling the amines to lower-alkyl acids, thereby coating the unprotected surface region of the particles with lower alkyl groups through amide linkages.

Following the reaction, the particles are released from the protective environment and washed, resulting in particles with reactive surface groups (in this case amine groups) only on the protected surface region of the particle. In this example, the protected area is adjacent the particle's south magnetic pole. It will be appreciated that the protected region of the particle, with respect to the particle magnetic poles, can be preselected merely by shifting the orientation of the magnetic field applied to the particle.

Figure 8B:
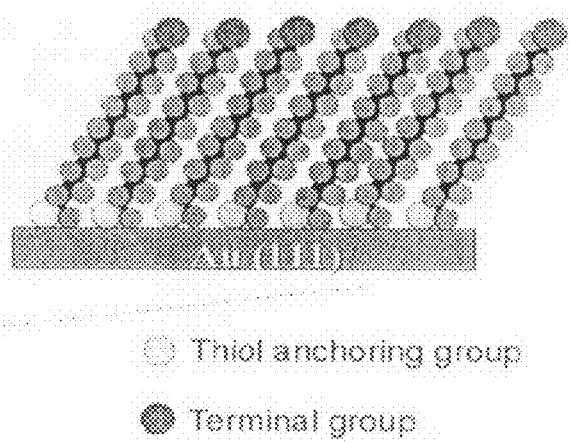

With continued reference to FIGS. 8A and 8B, hydrocarbon chains of a given chain length, and terminating in thiol groups, are allowed to react in solution with a surface containing a gold layer. Reaction of the thiol group with the gold layer is effective to couple the chains to the surface to produce a hydrocarbon chain monolayer, as shown in the bottom panel of FIG. 8A and in FIG. 8B.

In an exemplary method, a 1 to 2 mM solution of alkanethiolate in ethanol is added to a clean gold surface, whereupon the thiol moiety binds to the gold surface and forms a self-assembled monolayer (Nuzzo, R. et al. *J. Am. Chem. Soc.* 1983, 105:4481-83). Multilayers typically do not form, although adsorption times of several days may be necessary to form high-quality monolayers. Using alkanethiolate mixtures of differing carbon chain length introduces crystal defects that allow mobility of the chains, and should therefore increase the surface resiliency.

The force pressing a particle down into such an alkyl-thiol-gold monolayer and the force causing migration of the particles to the inner surface of a measurement cuvette can be calculated using the strength of the magnetic field gradient and the magnetic moment of the particle. For example, the translational force exerted on a magnetic particle by a magnetic field is given by the equation (Scherer, C. and Figueiredo, A. *Braz. J. Phys.*, 2005: 35:3a):

$$F = M \cdot \nabla B$$

where M is magnetic moment and $\nabla B$ is field strength gradient. Therefore, translational force is linearly proportional to the gradient field.

Using the solenoid equation described below (i.e., Section VI. C.) the field strengths produced by the solenoid at two nearby points near one end (i.e., where the gradient is strongest) are:

$$z_0 = 12.0 \text{ mm} \rightarrow B_z(z_0) = 1.839 \text{ mT and } z_0 = 13.0 \text{ mm} \rightarrow B_z(z_0) = 1.756 \text{mT}$$

Therefore, the gradient $\nabla_B$ is:

$$(1.839 \text{ mT} - 1.756 \text{ mT})/(0.013 \text{ m} - 0.012 \text{ m}) = 83.00 \text{ mT} \cdot \text{m}^{-1}$$

and the linear force on the particle is $$(1.043 \times 10^{-14} \text{ A} \cdot \text{m}^2) \cdot (8.300 \times 10^{-2} \text{ N} \cdot \text{A}^{-1} \cdot \text{m}^{-2}) = 8.657 \times 10^{-16} \text{ N} = 8.657 \times 10^{-16} \text{ kg} \cdot \text{m} \cdot \text{s}^{-2}$$

This is the force pressing the particle down into the alkyl-thiol-gold monolayer (or polymer sheet, fluid interface, etc.), and also the force causing migration of the particles to the inner surface of a measurement cuvette.

A larger gradient can be obtained by using a neodymium magnet. A N48 neodymium magnet has a remnant induction of 1.38 Tesla. Using an algorithm provided by Arnold Magnetics (i.e., calculation of field near a permanent magnet) for a cylindrical magnet 10 mm thick and 50 mm diameter the field strength is 0.2503117 T at 1 mm above the surface center, and 0.2496704 T at 1.1 mm above the surface center. This gives a gradient of 6.413 T·m$^{-1}$ and a force of 6.689× 10$^{-14}$ N. For a cylindrical magnet 2 mm thick and 5 mm diameter, the field strength is 0.2738131 T at 1 mm above the surface center, and 0.2592156 T at 1.1 mm above the surface center. This gives a gradient of 145.975 T·m$^{-1}$ and a force of 1.523×10$^{-12}$ N.

Figure 9D:
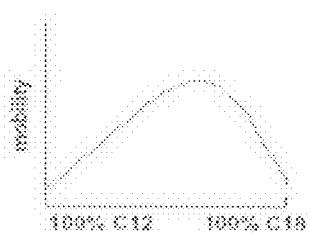
FIG. 9D shows is a plot of monolayer mobility (or resilience) as a function of chain length and heterogeneity.
Figure 9A:
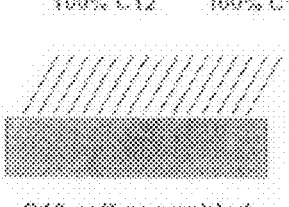
FIGS. 9A-9C show monolayer hydrocarbon films with relatively short (9A), mixed (9B), and relatively long (9C) chains.
Figure 9B:
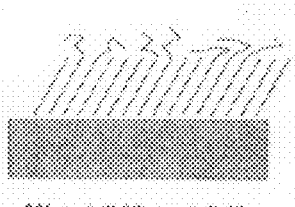
Figure 9C:
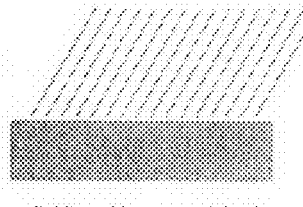

The depth that a particle will penetrate into an alkyl monolayer (and thus the degree of protection of its embedded surface amines) will be determined by the deformation force required for the alkyl monolayer. These considerations also apply to the polymer layers, solution interfaces, and the like. FIGS. 9A-9C illustrate three monolayers formed with relatively short (C12) chains (FIG. 9A), relatively long (C18) chains, and a mixture of the two different-length chains (FIG. 9B). The mobility or resilience of the three monolayers is plotted in FIG. 9D. Maximum resilience is achieved with a mixture of chain lengths, consistent with the model in FIG. 9B, in which the density of chains, above the shortest chain length, decreases with heterodispersity of the chain lengths.

Since the torque experienced by a particle is dependent on the angle between the external field and the particle's field, all particles will become coherent, as long as the phase shift $\phi$ does not exceed 90° (e.g., the frequency is not pushed above 309.2 Hz for 1000 nm diameter maghemite particles in protoplasm).

Other methods for selectively activating or deactivating preselected surface regions of magnetic particles can be used. For example, the particles could be magnetically oriented at the interface of a two-phase liquid system in which (i) the depth of penetration of the particles into the lower medium would rely on the relative densities of the particles and liquid phases, and applied field strength, and the selected reaction would be carried out in one of the two phases only, e.g., in a lower aqueous phase.

In still another method, the particles are oriented against a protective surface in a plasma chamber, and then exposed to a plasma, e.g., generated in the presence of oxygen, using known conditions for surface modification by plasma treatment. In one embodiment, for example, a particle coated with amine groups is exposed to a plasma effective to remove the amine groups or oxidize them to nitrate groups, leaving free amine groups only at the surface protected portion of the particle.

The particles may also be oriented in an environment wherein a preselected portion of the particles is caused to contact a solution, suspension, or deformable layer in which the indicated chemical reagents are disposed, thereby allowing the select modification of the preselected portions of the particles (see also, Section III.E., below).

B. Specific Composition Chemistry

As described above, magnetic particles are selectively activated or deactivated by employing a magnetic field to orient the particles in an environment in which a portion of each particle surface is exposed to a selected environment and the remainder portion is shielded from such environment.

Following activation/deactivation (if required), the magnetic particle is then attached (i.e., coupled), directly or indirectly, to one or more fluorescence detectable moieties. Fluorescent dyes and other fluorescence detectable compounds are commercially available from such companies as Gene Link (Hawthorne, N.Y., USA), Invitrogen (Carlsbad, Calif., USA), Analytical Imaging Facility (Bronx, N.Y., USA), Risk Reactor (Huntington Beach, Calif., USA), and Foray (San Diego, Calif., USA). Fluorescence detectable compounds having numerous different emission spectra are available, including but not limited to red, green, blue, yellow, orange, and violet.

A variety of chemical coupling reactions are known for covalently coupling particle or molecular reagents (i.e., components) to one another may be employed in the method. In one embodiment, the covalent coupling is direct chemical coupling between amine groups carried on the magnetic particles and acid groups carried on the fluorescence detectable moieties, to covalently attach the two components through an amide linkage. Linkage through ester, ether, carbamate, disulfide, or other chemical bonds may be carried out according to well-known chemical-coupling methods. Alternatively, the chemical groups on the two components may be linked through a bifunctional coupling reagent.

Figure 10:
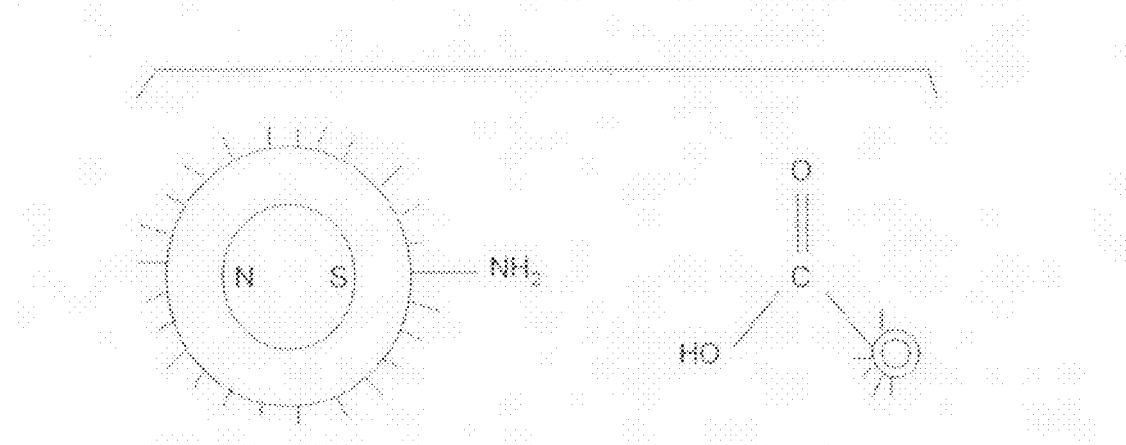
FIG. 10 illustrates the components of one type of magnetic particle composition, shown aligned with the magnetic poles in a magnetic particle.
Figure 11:
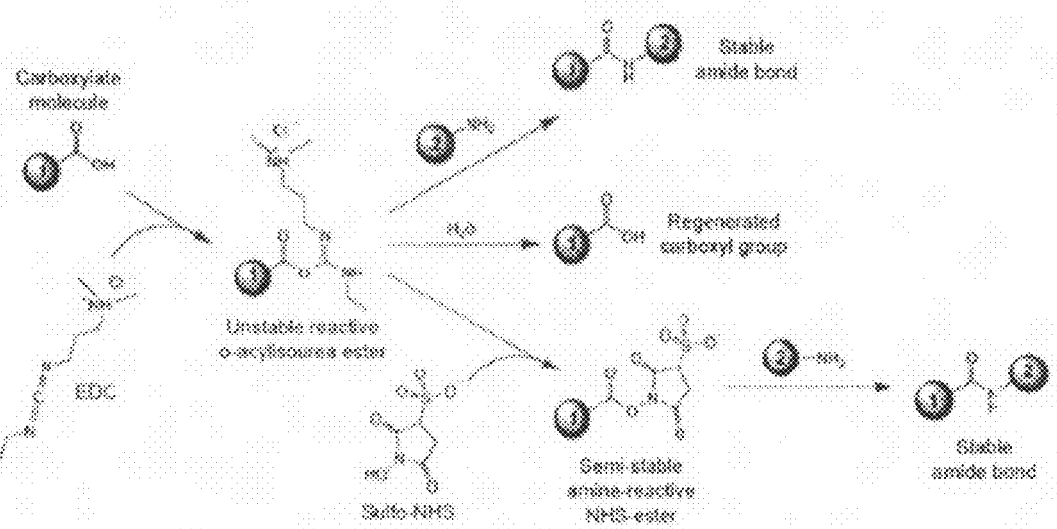
FIG. 11 shows steps in the attachment of magnetic and quantum dots.

FIG. 10 illustrates an exemplary approach, where the preselected regions of the magnetic particles (left) are coated with free amine groups, and the fluorescence detectable moieties (right) are coated with carboxyl groups. A typical linking reaction is illustrated in FIG. 11, where 1-Ethyl-3-[3-dimethylaminopropyl]carbodiimide hydrochloride (EDC or EDAC), a zero-length cross-linking agent, is used to couple carboxyl groups to primary amines (Grabarek, Z. and Gergely, J. *Anal. Biochem.* 1990, 185:131-35; Staros, J. et al. *Anal. Biochem.* 1986, 156:220-22). In other embodiments, magnetic particles are coated with carboxyl groups and fluorescence detectable moieties are coated with amine groups.

Covalent linkage between the magnetic particles and fluorescence detectable moieties includes indirect covalent linkage where a ligand in a ligand/anti-ligand pair is attached to a particle, and the anti-ligand to the fluorescence detectable moiety (or vice versa), with the ligand/anti-ligand interaction serving to link the two components. Thus, for example, biotin may attached or coupled (e.g., covalently) to the magnetic particles, and avidin to the fluorescence detectable moieties, allowing the particles and fluorescence detectable moieties to be linked via avidin binding to biotin. In another embodiment, avidin is attached to the particles. Similar results may be obtained using, for example, corresponding antibodies and antigens, or fragments, thereof.

In some embodiments, magnetic particles are attached to a plurality of fluorescence detectable moieties. A plurality of moieties refers to 2, 3, 4, 5, 6 or more fluorescence detectable moieties. In preferred embodiments, each fluorescence detectable moiety has a unique absorption. and/or emission spectrum (i.e., "emission color") such that the same fluorescence detectable moiety-labeled magnetic particle may be used with different wavelengths of excitation energy. Several embodiments of the present magnetic particle compositions, which include a plurality of different fluorescence detectable moieties, are depicted in FIGS. 12A-12F.

Figure 12:
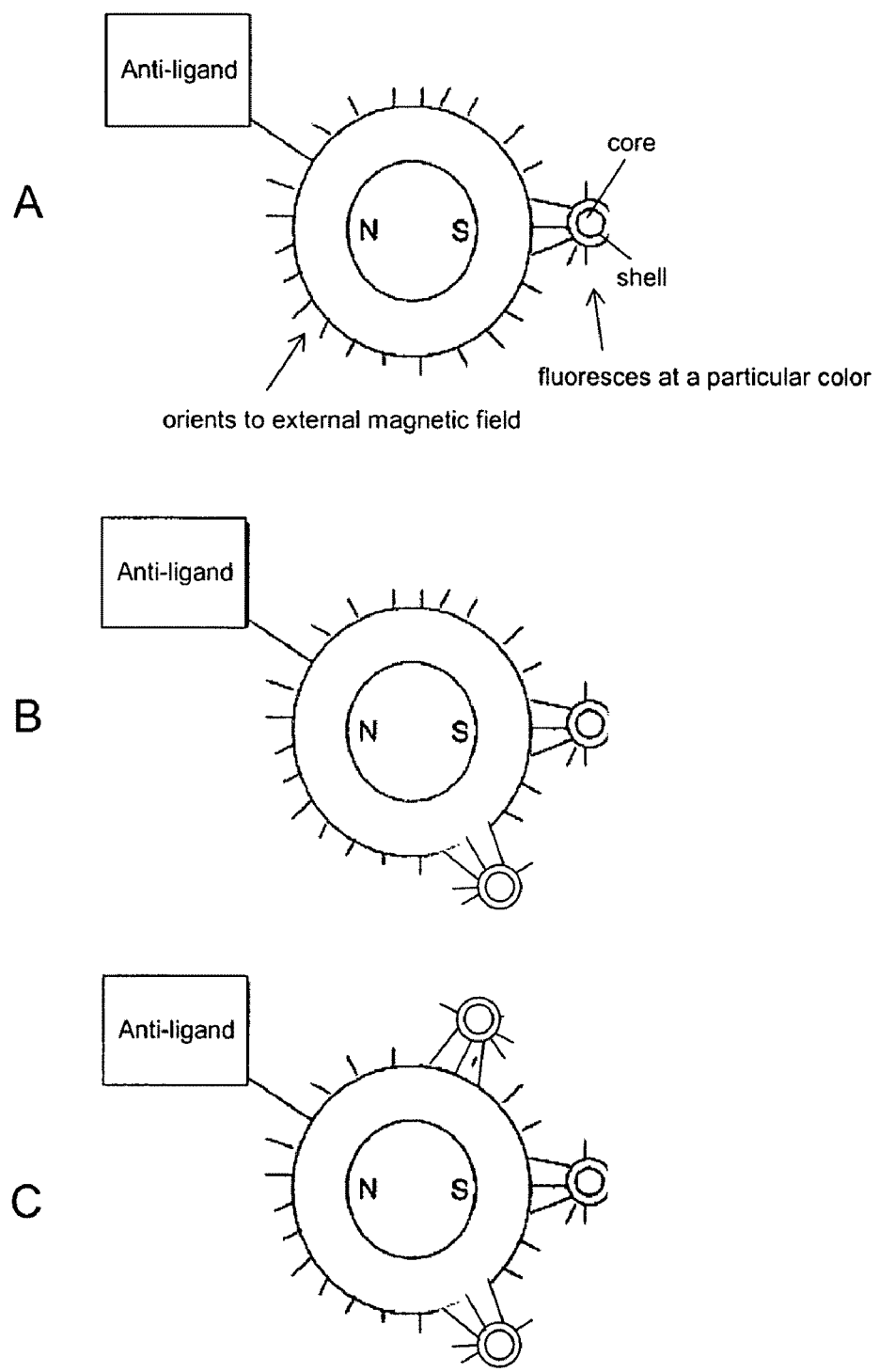
FIGS. 12A-12F show exemplary magnetic particle compositions having (A) a single fluorescence detectable moiety and a single assay reagent/anti-ligand, (B) two different fluorescence detectable moieties and a single assay reagent/anti-ligand, (C) three different fluorescence detectable moieties and a single assay reagent/anti-ligand, (D) a single fluorescence detectable moiety and two different assay reagents/anti-ligands, (E) two fluorescence detectable moieties and three different assay reagents/anti-ligands, and (F) three fluorescence detectable moieties and two different assay reagents/anti-ligands, one fluorescence detectable moiety and one assay reagent/anti-ligand is attached to the magnetic particle via linkers/spacers. Another fluorescence detectable moieties is attached to an additional terminal group.
Figure 12:
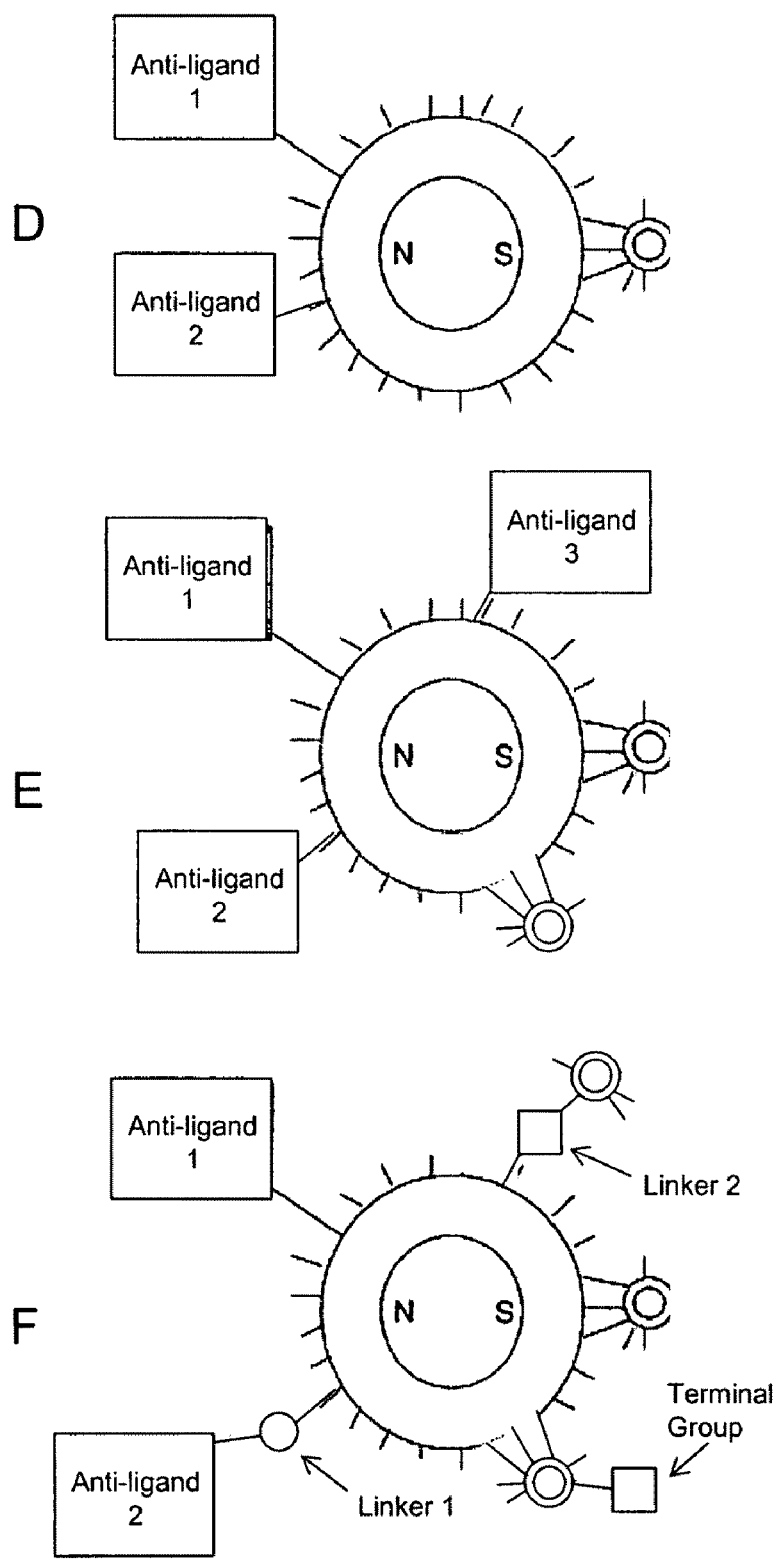

In some embodiments, it may be desirable to include a linker (or spacer) molecule between the fluorescence detectable moiety and the magnetic particle, e.g., to increase the mass of the quantum dot-linker complex, to reduce interactions between the particles and the quantum dots, to avoid interfering with ligand-anti-ligand interactions, to improve fluorescence detection, to reduce interactions between adjacent magnetic particle compositions (i.e., "chaining"), or to add functionality. This embodiment is shown in FIG. 12F. The linker is preferably a non-magnetic entity (i.e., functional group, polymer, particle, etc.). FIG. 12F also shows a terminal group added to a fluorescence detectable moiety, which can also be used to increases mass, increase drag, reduce chaining, add functionality, etc., as in the case of the linker.

In some embodiments, a single fluorescence detectable moiety of any given emission color is attached to each magnetic particle. The use of a single emission color fluorescence detectable moiety on each magnetic particle increases the ability to detect particle rotation or movement. Preselected magnetic particle:fluorescence detectable moiety ratios can be achieved by controlling the concentration of components during attachment or by size-selecting the population of products obtained following attachment of fluorescence detectable moieties. Magnetic beads that are not attached to fluorescence detectable moieties are generally invisible to the detection device (below) and do not interfere with analyte detection.

In other embodiments, a plurality of the same emission color fluorescence detectable moieties are attached to each magnetic particle, preferably grouped together such that particle rotation can be visualized by measuring a change in fluorescence. In such cases, it may be desirable to size-select a population of the resulting magnetic particle-fluorescence detectable moieties, such that a uniform population is obtained. A uniform population of fluorescence detectable moiety-labeled particles provides less noise and sharper peaks than a mixed population.

In yet further embodiments, a plurality of different emission color fluorescence detectable moieties are attached to the same magnetic particle. This embodiment is illustrated in FIGS. 12A-12F, which show particles with one (FIGS. 12A and 12D), two (FIGS. 12B and 12E), and three (FIGS. 12C and 12F) different fluorescence detectable moieties. Particles may) also have, 4, 5, 6, or more fluorescence detectable moieties, provided that they do not interfere with ligand-antiligand interactions.

Figure 22:
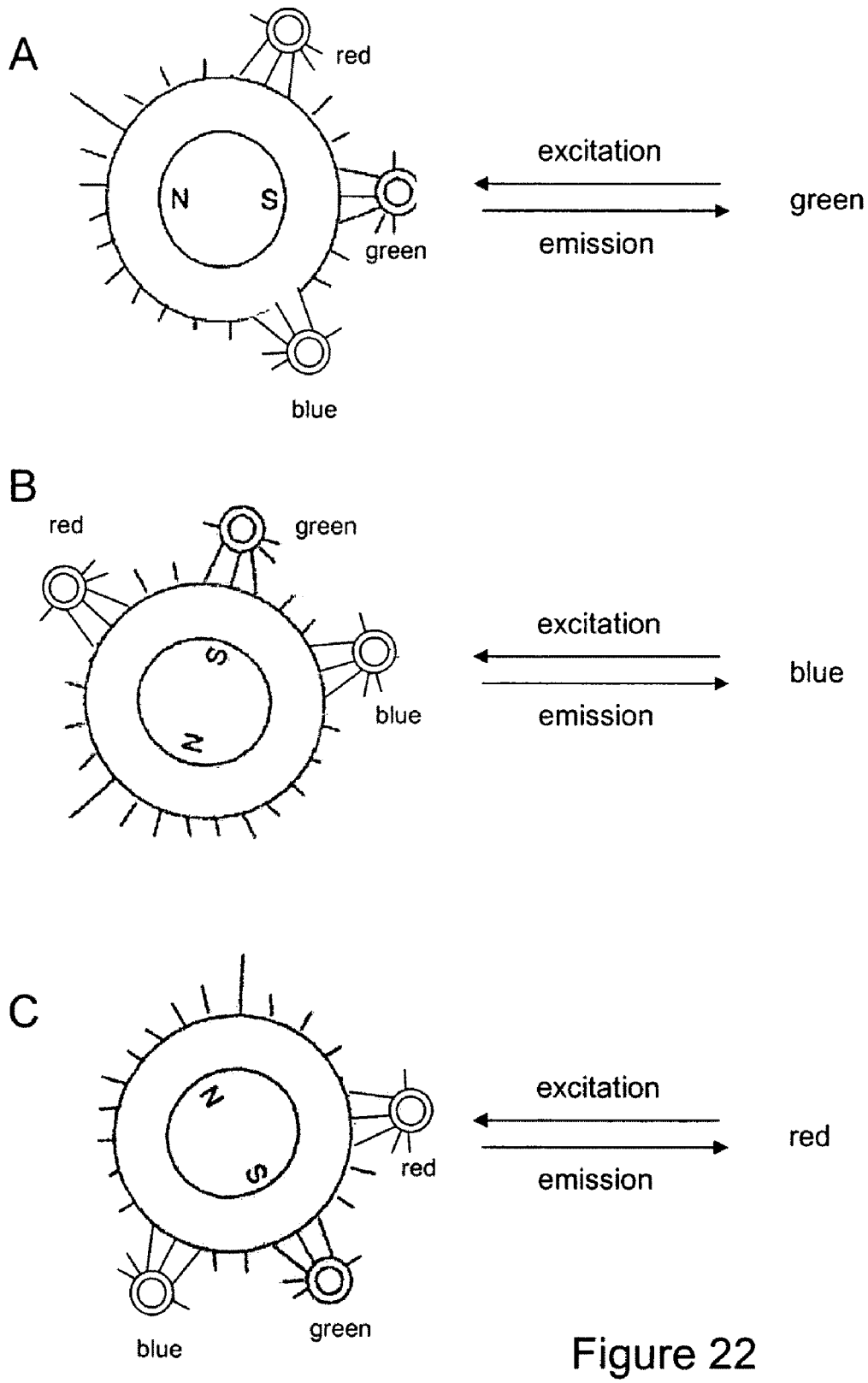
FIGS. 22A-22C show a magnetic particle with three fluorescence detectable moieties aligned in magnetic fields having each of three different directions.
FIG. 22D depicts a matrix display or screen comprising a population of magnetic particles.
Figure 22:
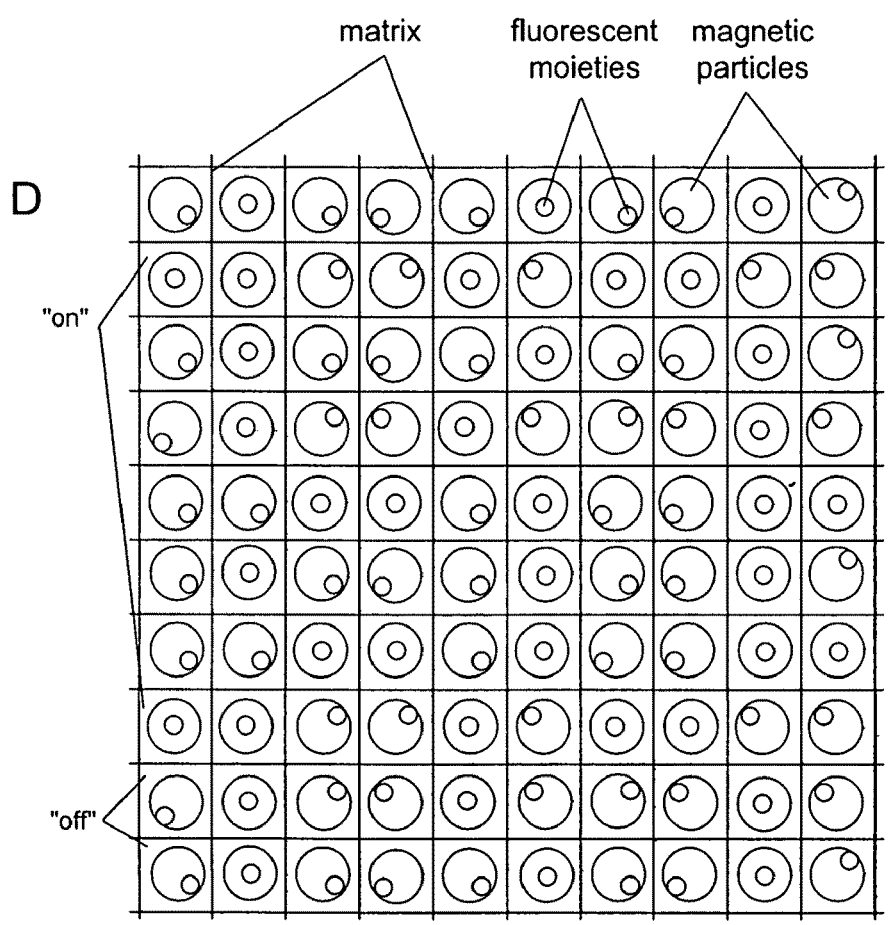

In some embodiments, a single fluorescence detectable moiety of each emission color is attached to the particle. In other embodiments, a plurality of each emission color fluorescence detectable moiety is used, in which case size selection may be used to obtain a uniform population. The plurality of each emission color fluorescence detectable moiety should be localized to single region of the particle such that the fluorescence signal varies when the particles are moved or rotated in a magnetic field.

Where different color fluorescence detectable moieties are attached at different preselected positions on the particle, the alignment of the particle in a magnetic field may result in one population of fluorescence detectable moieties being exposed to external excitation energy from a given direction, while another population is shielded (or less directly affected by) the excitation energy. This situation is shown in FIGS. 22A-22C, The exemplary magnetic particles include fluorescence detectable moieties of red, green and blue, although other combinations of colors can be used. Changing the direction of the magnetic field changes the orientation of the particles, such that a photodetector in a given position (arrows) detects a different emission color depending on the direction of the magnetic field. In a first orientation, only the green emission color fluorescence detectable moiety visible to the detector (FIG. 22A). In a second orientation, only the blue emission color fluorescence detectable moiety is visible to the detector (FIG. 22B). In a third orientation, only the red emission color fluorescence detectable moiety is visible to the detector (FIG. 22C). In other positions, a combination of the fluorescence detectable moieties, or no fluorescence detectable moieties, is visible to the detector (not shown).

In this manner, the compositions of the invention can be used to alter the observed optical properties of a solution, suspension, or other material comprising magnetic particle:fluorescence detectable moiety composition, by changing the direction of the magnetic field to which the particles are exposed, and monitoring the emission color from a given angle/direction. Where magnetic particle compositions are arranged in a matrix in which the orientation of each particle (or a subpopulation of particles) can be independently controlled by changing the direction of a external magnetic fields, the matrix can be used to produce an image in which each particle (or subpopulation of particles) is equivalent to a pixel in a computer screen or television monitor (as shown in FIG. 22D).

C. Quantum-dot Particles

Quantum dot particles (or quantum dots, QDs) are available from such suppliers as Evident Technologies, Inc. (Troy, N.Y., USA) and Invitrogen, Inc. (Carlsbad, Calif., USA). QDs are well suited for use as fluorescence detectable moieties attached to magnetic particles, as described herein.

QDs are typically 3 to about 10 nm in diameter and contain 100s to 1000s of atoms. They are composed of a fluorescing core, a protective shell, an inner coating, an outer coating, and then a ligand coating. The core is typically CdS (UV-blue), CdSe (visible), or CdTe (red-IR), and exhibits high photon absorption (10×-1,000× more than dyes) and exhibits quantum yields of 30% to 50%, which is equivalent to the most fluorescent dyes currently available.

QDs exhibit strong fluorescence from 465 nm to 2,300 nm with full spatial width at half-maximal fluorescence (FWHM) of 30 nm. The absorption band of quantum dots is much broader than for organic dyes. The emission color can be fine-tuned by changing the core diameter. The shell is typically ZnS to bypass non-fluorescing energy traps and for chemical stability. The inner coating typically consists of organic ligands to further stabilize the core and form a base for the outer coating. The outer coating is typically a mixed hydrophobic/hydrophilic polymer with carboxylic acid derivatization. The hydrophobic portion interacts with the inner coating, and the hydrophilic portion provides solvent solubility and a carboxylate surface to which biological and non-biological ligands can be attached. FIG. 5 illustrates features of a typical quantum dot.

The broadness of absorption peaks (FIG. 6A) and the narrowness of emission peaks (FIG. 6B) suggest that several or many different colors can be used simultaneously. Since quantum dots are physically much more stable than dyes, the colors will not bleach. The fluorescence lifetime is 15-20 ns, which is about 10 times longer than organic dyes.

When the fluorescence detectable moieties are quantum dots, the addition of EDC (e.g., as described in Section III.B., above) forms an unstable amine-reactive O-acylisourea intermediate. This intermediate can react with an amine on a magnetic particle, yielding components joined by a stable amide bond. In aqueous solution, the intermediate can also react with water, hydrolyzing to reform the carboxyl group and negatively impacting the efficiency of amide bond formation. This hydrolysis can be avoided by the addition of Sulfo-NHS to stabilize the amine-reactive intermediate by converting it to an amine-reactive Sulfo-NHS ester. The NHS ester is sufficiently stable to avoid reacting with water, but still retains sufficient reactivity to form an amide bond at a reasonable rate.

The reaction rate between amine moieties on magnetic particles and carboxylate moieties on QDs is attenuated by slow particle diffusion rates, compared with reactions between freely dissolved amine molecules and carboxylate moieties on quantum dots. The mass of a quantum dot is about 4,000-times that of a free carboxylate molecule, and so its diffusivity to a (relatively immobile) magnetic particle can be crudely estimated to be $\frac{1}{4,000}^{th}$ that of the diffusion of free amine molecules to a (relatively immobile) quantum dot.

Thus, the reaction rate for derivatizing magnetic particles with quantum dots is expected to be 4,000-times slower than for derivatizing magnetic particles with free fluorescence detectable moieties. Protocols for such EDC-mediated reactions require about 1 hour. By extrapolation, efficient magnetic particle-quantum dot attachment could require 4,000 hours (referring to, e.g., published protocols provided with Invitrogen and/or Evident products).

However, diffusion of the reacting magnetic particles and quantum dots away from each other is also slower, allowing more time for nearby components to react than if they were able to rapidly diffuse away as unreacted free molecules. This suggests that less than 4,000 hours is required.

Moreover, the concentrations used in the commercial protocols are about 50 mg/mL quantum dot at room temperature. To achieve a faster reaction, concentrations can be increased 10× to 500 mg/mL, producing essentially a slurry of particles, and reducing the reaction time to about 400 hours. The reaction can be warmed by 20° C. Since this is a binary reaction, the reaction rate will approximately double for every 10° C. temperature increase, reducing the reaction time to a more reasonable 100 hours.

The reaction rate can also be increased by avoiding the use of Sulfo-NHS and performing the reaction in a non-aqueous solvent such as ethanol. The Sulfo-NHS reagent is used commercially to inhibit unwanted side-reactions with water, and produces a complex that is slower-reacting than the EDC complex.

Lastly, the reaction need not run to completion; even if some magnetic particles are not paired with fluorescence detectable moieties, the population of magnetic particles can still be used to detect analytes.

Covalent linkage between quantum dots and magnetic particles may be indirect, e.g., via a linkage where a ligand in a ligand/anti-ligand pair is attached to a particle, and the anti-ligand to the fluorescence detectable moiety (or vice versa), with the ligand/anti-ligand interaction serving to link the two entities. Examples of suitable ligand/anti-ligand pairs include antibodies and antigens, biotin and avidin, receptors and ligands, etc., as described herein.

In some embodiments, it may be desirable to include a linker (or spacer) molecule between a quantum dot and a magnetic particles, e.g., to increase the mass of the composition, to reduce interactions between the particles and the quantum dots, to avoid interference with ligand-anti-ligand interactions, to reduce interactions between adjacent magnetic particle compositions (i.e., "chaining"), to improve fluorescence detection, or to add functionality. FIG. 12F also shows a further embodiment in which terminal group added to a fluorescence detectable moiety. The terminal group can also be used to increases mass, increase drag, reduce chaining, add functionality, etc.

In some embodiments, a single quantum dot of any given emission color is attached to each magnetic particle. The use of a single quantum dot attached to each magnetic particle increases the ability to detect particle rotation or movement. This ratio can be achieved by controlling the concentration of the magnetic particles and quantum dots during attachment or by size-selecting magnetic particles following attachment of quantum dots. Magnetic beads that are not attached to a quantum dot are generally invisible to the detection device (below) and do not interfere with analyte detection.

In other embodiments, a plurality of the same emission color quantum dots are attached to each magnetic particle, preferably grouped together such that particle rotation can be visualized by measuring fluorescence. In such cases, it may be desirable to size-select a population of the resulting magnetic particle-quantum dot compositions, such that a uniform population is obtained. A uniform population of quantum dot-labeled particles provides less noise and sharper peaks than a mixed population.

In yet further embodiments, a plurality of different emission color quantum dots are attached to the same magnetic particle. This embodiment is illustrated in FIGS. 12A-12F, which show particles with one (FIGS. 12A and 12D), two (FIGS. 12B and 12E), and three (FIGS. 12C and 12F) different quantum dots. Particles may also have 4, 5, 6, or more quantum dots, provided that the number of quantum dots does not interfere with ligand-anti-ligand interactions.

Where only a single QD of each emission color is attached to each magnetic particle, the quantum dots may be localized to a single region of the particle or distributed over different regions. In other embodiment, a plurality of each quantum dot is used, which should be localized to a preselected region of the particle. Size selection can be used to obtain a uniform population.

Where different color quantum dots are attached at different preselected positions on the particle, the alignment of the particle in a magnetic field may result in one population of quantum dots to being exposed to excitation energy, while another population is shielded from excitation energy. This embodiment is shown in FIGS. 22A-22C. The magnetic particles include quantum dots of e.g., red, green and blue. Changing the direction of the magnetic field changes the orientation of the particles, such that a photodetector positioned according to the arrows detects a different signal depending on the orientation of the magnetic particles. In a first orientation, only the green quantum dot is visible to the detector (FIG. 22A). In a second orientation, only the blue quantum dot is visible to the detector (FIG. 22B). In a third orientation, only the red quantum dot is visible to the detector (FIG. 22C). In other positions, a combination of the quantum dots, or no quantum dots, is visible to the detector (not shown). In this manner, the compositions of the invention can be used to alter the observed optical properties of a solution, suspension, or other material comprising such dots, by changing the direction of the magnetic field to which the particles are exposed. A matrix display or screen comprising a population of particles is shown in FIG. 22D.

D. Assay Reagents/Anti-ligands

In some embodiments, the magnetic particles may be modified, before or after attachment of fluorescence detectable moieties, to include one or more assay reagents, or anti-ligand molecules. Anti-ligand molecules are capable of binding specifically with ligand molecules (or analytes) to which the composition is exposed in solution. Typical ligand reagents include enzymes, antigens, receptor binding agents, and nucleic acid molecules of known base sequence.

The chemistry used for coupling the reagent to the particles is preferably orthogonal to that used for coupling of the quantum-dot particles. For example, where an amide linkage is used for fluorescence detectable moiety attachment, the assay reagent may be attached through a thiol or disulfide linkage, such that the fluorescence detectable moiety is not perturbed by attachment of the assay reagent, or vice versa.

Figure 13:
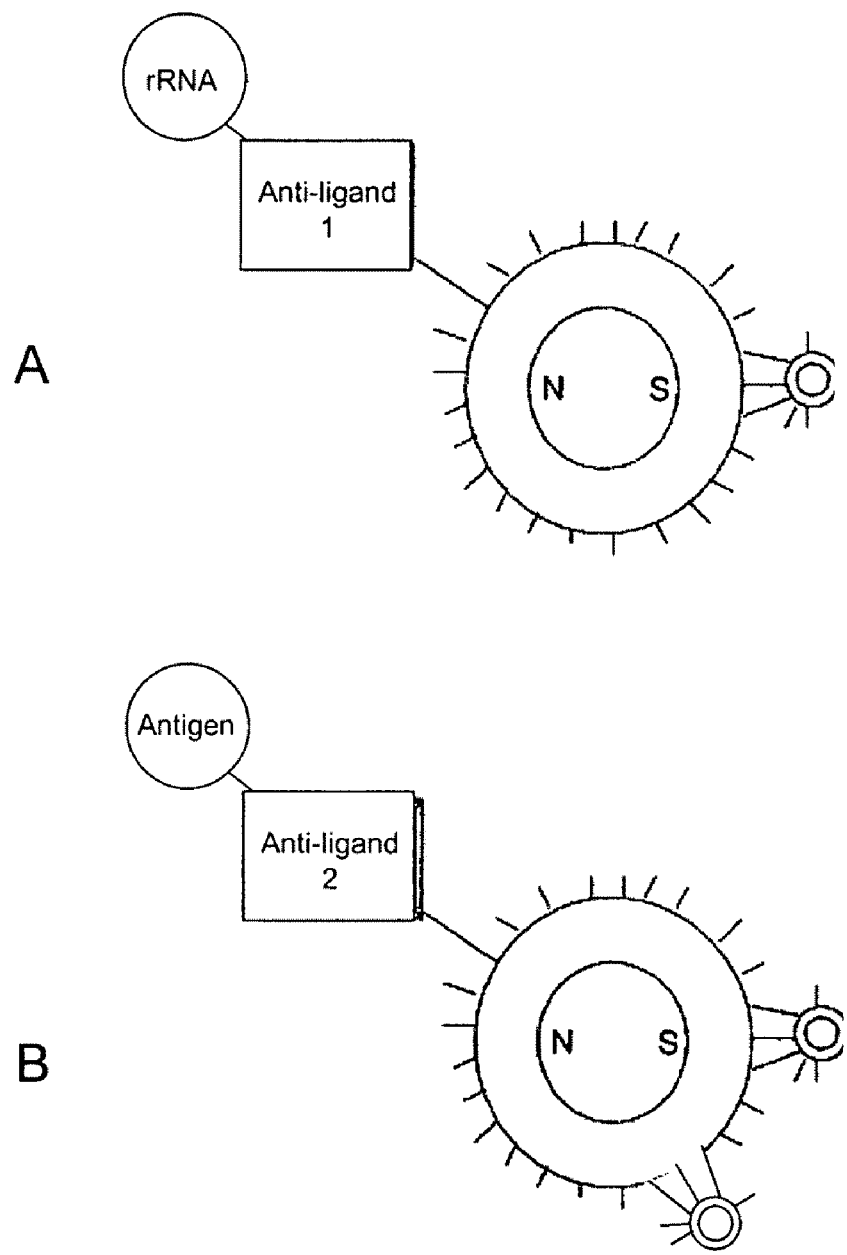
FIGS. 13A and 13B show exemplary magnetic particle compositions attached to their cognate ligands, illustrated by (A) rRNA and (B) an antigen.
Figure 17A:
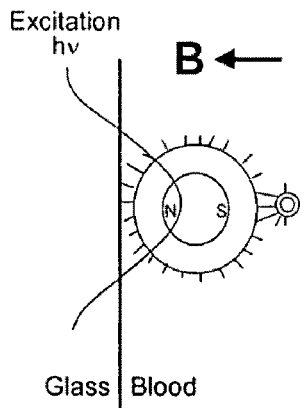
FIGS. 17A and 17B illustrate evanescent fluorescence excitation events in a rotating composition.
Figure 17B:
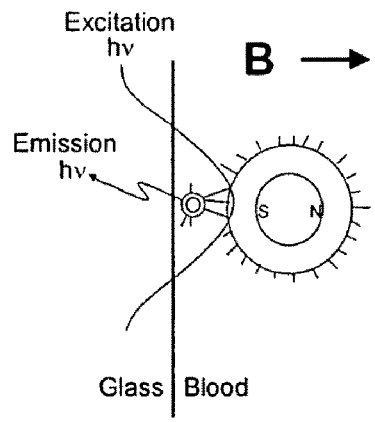
Figure 18:
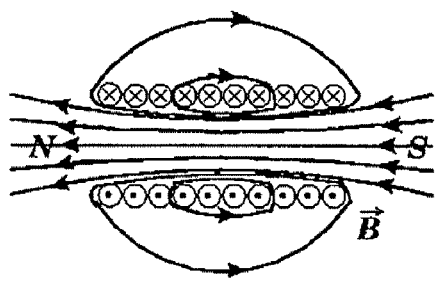
FIG. 18 is a cross-sectional view showing magnetic fields and forces produced in a solenoid activated with an alternating current.

FIGS. 12A-12F show a number of embodiments of the present magnetic beads having a single assay reagent (anti-ligand; i.e., FIGS. 12A-12C) or a plurality of different assay reagents/anti-ligands (i.e., FIGS. 12D-12F), along with a single fluorescence detectable moiety (i.e., FIGS. 12A and 12D) or a plurality of different fluorescence detectable moieties (i.e., FIGS. 12B, 12C, 12E, and 12F). FIGS. 13A and 13B shown exemplary magnetic particle compositions bound to different exemplary ligands/analytes, i.e.,(A) rRNA and (B) an antigen.

In some embodiments, each magnetic particle comprises a single anti-ligand molecule having a particular specificity (e.g., as shown in FIGS. 12A-12C, 13A, and 13B). In other embodiments, each magnetic particle comprises a single anti-ligand molecule of each of a plurality of anti-ligand molecules having different specificities (e.g., as shown in FIGS. 12D-12F).

In still further embodiments, a magnetic particle comprises a plurality of anti-ligand molecule having a particular specificity or a plurality of anti-ligand molecules having different specificities. In such cases, it may be desirable to size-select a population of the resulting magnetic particle-anti-ligand compositions, such that a uniform population is obtained. A uniform population of anti-ligand-labeled particles provides less noise and sharper peaks than a mixed population.

As described below (e.g., Section IV), the binding of analyte to a resulting magnetic particle composition affects rotation in an alternating or rotating magnetic field, and this rotation can be detected by the changes in the phase angle of fluorescence emission of the particle, and through occultation.

E. Physically Attaching Fluorescence Detectable Moieties and Anti-ligands

In some embodiments, fluorescence detectable moieties and/or anti-ligands are physically attached to preselected regions of magnetic particles. For example, fluorescence detectable moieties (including quantum dots) can be attached by aligning the magnetic particles in a magnetic field contacting a preselected portion of the aligned particles with a solution, suspension, or semi-solid composition comprising fluorescence detectable moieties.

Figure 20:
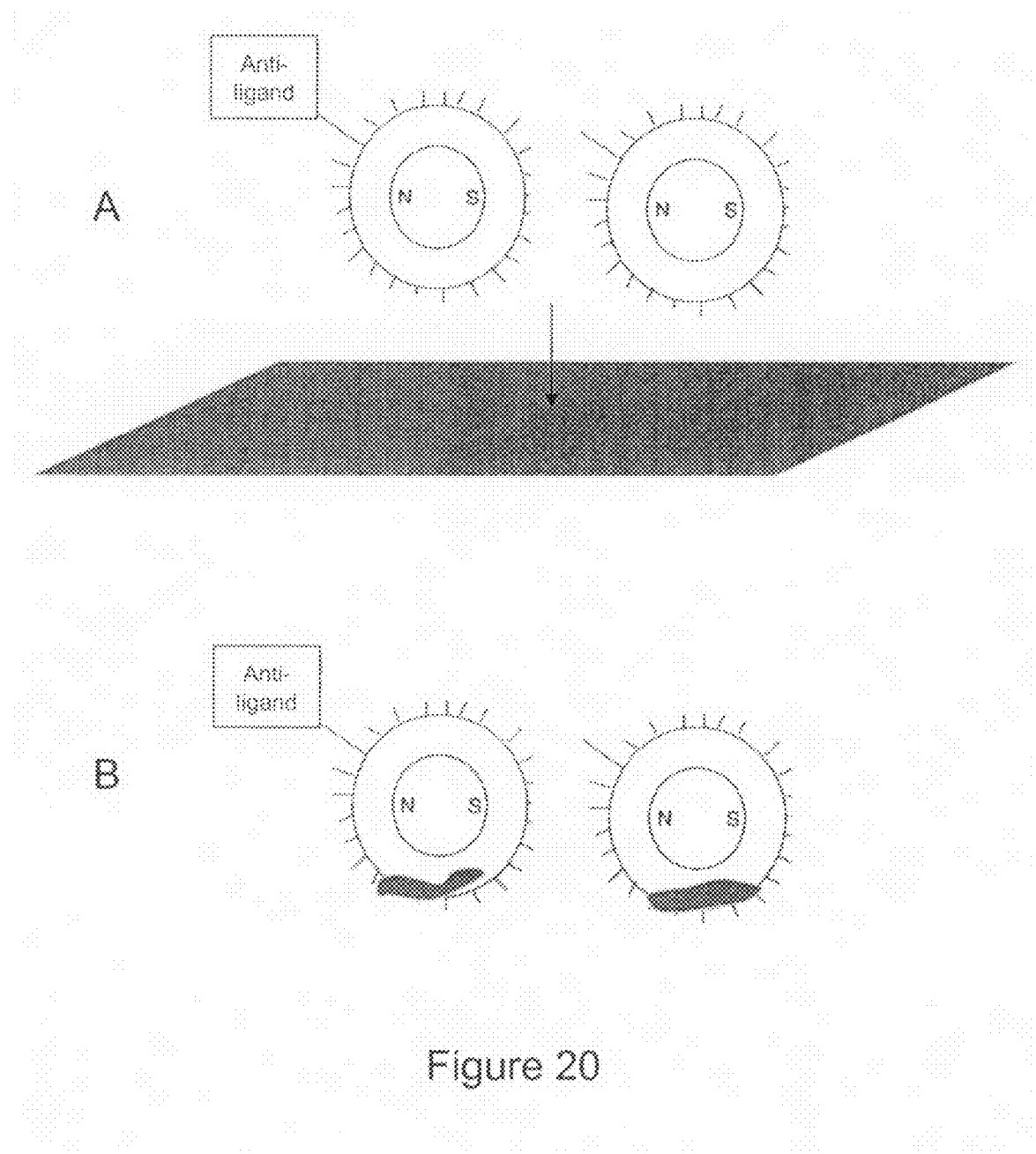
FIGS. 20A-20B illustrate aspects of the "dipping" method for physically attaching fluorescence detectable moieties (or anti-ligands) to preselected regions of magnetic particles. Magnetic particles are shown aligned and ready to "dip" in FIG. 20A. The resulting particles are shown in FIG. 20B.

FIG. 20A shows magnetic particles aligned in a magnetic field, and in contact with a polymeric composition comprising fluorescence detectable moieties. The magnetic particles and/or the polymer composition are then heated to melt the polymer, causing the physical transfer of an amount of the polymer (and fluorescence detectable moieties) to adhere to a preselected area of the particles. The resulting particles are shown in FIG. 20B, with an amount of the fluorescence detectable moiety transferred to the predetermined region of the particles. Assay reagents/anti-ligands can be attached before or after this "dipping" procedure.

Related embodiments use a solution, suspension, fluid interface, or semi-deformable material comprising fluorescence detectable moieties rather than a polymeric material. Lipid materials may also be used. The solution, suspension, polymeric or other material in which the particles are in contact may harden on the particle or react with the particle, thereby depositing an amount of fluorescence detectable moieties on the particles. Alternatively, the particles may be removed from contact with the solution or suspension and the residual amount remaining on the particles is allowed to dry. Heating, cross-linking, or chemical steps may be performed to cause the fluorescence detectable moieties to attach to the particles (as in Sections III.B. and III.C.).

In some embodiments, a polymeric or other surface is adapted with wells, pockets, or recesses comprising a solution, suspension, or other form of fluorescence detectable moieties, and the aligned particles engage these wells, pockets, or recesses. In further embodiments, magnetic particles are aligned in a close-packed arrangement one a surface in a plasma chamber, and the exposed surface is modified by plasma treatment. The particles may also be aligned and one surface irradiated, printed, spray-painted, or otherwise coated with fluorescence detectable moieties.

Note that the "dipping" method, and related embodiments, can be used to activate the magnetic particles, attach specific chemistries (including fluorescence detectable moieties, such as dyes and quantum dots), attach assay reagents/anti-ligands, or combinations, thereof. Particles can be "dipped" in a solution, suspension, or polymeric composition comprising a single fluorescence detectable moiety or anti-ligand, a plurality of fluorescence detectable moieties or anti-ligands, or variations, thereof. The particles may also be brought into contact with a deformable surface or an array of pockets in which a magnetic particle can be cradled. Such pockets (or wells) may contain a polymer suspension or a coating of polymer chains.

In all cases, the derivatized magnetic particles may be size/mass-selected to increase uniformity, e.g., using chromatographic or electrophoretic procedures.

IV. Physics of Magnetic Particle Rotation and Occultation

The attachment of a ligand to an anti-ligand present on a magnetic particle changes the physical properties of the particle in a magnetic field as follows.

A. Rotation Frequency

Magnetic particle bound to analytes demonstrate a change in rotational frequency under the influence of a rotational field, compared to equivalent particles nor bound to analyte. Factors influencing rotational velocity are as outlined in the discussion below, with reference to FIGS. 14A, 14B, and 15.

For the purposes of the exemplary calculations, the viscosity of water is 1.0020 centiPoise at 20° C. (i.e., 0.010020 Poise) and the viscosity of cellular protoplasm is about 4 centiPoise, based on molecular diffusion studies (Freitas, R. A. Jr.; *Biofluid Viscosity, Nanomedicine, Volume I: Basic Capabilities*, 1999, Section 9.4.1.1. Landes Bioscience, Georgetown).

Since 100 centiPoise=1 g·cm$^{-1}$·s$^{-1}$=0.1 Pascal-second, and since 1 Pascal-second=1 N·s·m$^{-2}$=1 J·s·m$^{-3}$=1 kg·m$^{-1}$·s$^{-1}$, then the viscosity of protoplasm is 0.004 J·s·m$^{-3}$=0.004 kg·m$^{-1}$·s$^{-1}$.

A spherical particle in viscous suspension will experience a random rotation due to molecular collisions, called Debye or Brownian rotation. The relaxation time of this rotation is given by the equation (Scherer and Figueiredo, A. *Braz. J. Phys.* 2005, 35:3a):

$$t_B = (3 \cdot V \cdot n)/(k_B \cdot T)$$

where $t_B$ is the relaxation time (the mean time to rotate 1 radian), V is particle volume, n is the viscosity, $k_B$ is the Boltzmann constant, and T is the absolute temperature.

Assuming the volume of 1,000 nm diameter particle (including the shell) is $(4/3) \cdot \pi \cdot r^3 = 5.236 \times 10^{-19}$ m$^3$, the viscosity of protoplasm is 0.004 J·s·m$^{-3}$, $k_B$ is $1.3807 \times 10^{-23}$ J·K$^{-1}$, and T is 293 K, then $t_B$=1.55 s for 1 radian (rad) rotation of a 1,000 nm diameter particle in protoplasm.

Note that this value would actually be slightly larger (i.e., the rotation time longer) due to the attachment of a fluorescence detectable moiety, which in some embodiments is a 20 nm-diameter quantum dot.

B. Maqnetic Particle Torque Due to Brownian Motion

The moment of inertia for a uniform sphere is given by the equation:

$$I = (2/5) \cdot m \cdot r^2$$

where m is mass and r is the radius. For a 1,000 nm particle of approximate density=5000 kg·m$^{-3}$ (e.g., maghemite and silica), the mass would be m=2.618×10$^{-15}$ kg and therefore I=2.618×10$^{-28}$ kg·m$^2$.

The moment (torque) of the sphere is given by:

$$M = IR$$

where R is the angular acceleration as rad·s$^{-2}$.

Since R=1 rad/(1.55 s)$^2$=4.162×10$^{-1}$ rad·s$^{-2}$, then M=1.090×10$^{-28}$ kg·m$^2$·s$^{-2}$=1.090×10$^{-28}$ N·m due to Brownian motion in protoplasm on a 1,000 nm diameter particle.

C. Magnetic Particle Rotation and Torque Due to External Magnetic Field

For maghemite particles, the magnetic moment $J_{rs}$=31.42 A·m$^2$·kg$^{-1}$, density=5074 kg·m$^{-3}$, and the volume of a 500 nm diameter core is V=(4/3)·π·r$^3$=6.544×10$^{-20}$ m$^3$. Therefore the magnetic moment of a single particle is $$M = (6.544 \times 10^{-20} \text{ m}^3) \cdot (5074 \text{ kg·m}^{-3}) \cdot (31.42 \text{ A·m}^2 \cdot \text{kg}^{-1}) = 1.043 \times 10^{-14} \text{ A·m}^2$$

The torque on a spherical particle is given by the following equation (Reitz, J. et al. *Foundations of Electromagnetic Theory*, Third Edition, Addison-Wesley Publishing Co., 1980, pp. 165):

$$\text{Torque (N·m)} = \text{magnetic dipole moment (A·m}^2) \times B \text{ magnetic field (N·A}^{-1}\cdot\text{m}^{-1})$$

Thus Brownian motion causes twisting equivalent to a magnetic field strength of $$B = (2.179 \times 10^{-29} \text{ N·m})/(1.043 \times 10^{-14} \text{ A·m}^2) = 2.089 \times 10^{-15} \text{ N·A}^{-1}\cdot\text{m}^{-1} = 2.089 \text{ fT}.$$

The field strength near a conductor is given by the following equation (Reitz, F. J. et al. *Foundations of Electromagnetic Theory*, Third Edition, Addison-Wesley Publishing Co., 1980, pp. 168):

$$B = (\mu_0 \cdot I)/(2 \cdot \pi \cdot a)$$

where I is conductor current and a is the distance from the conductor. A single pyramidal cell generates 2×10$^{-11}$ A of current (Wikswo, J. et al. *Science* 1980, 208:53-55) which results in a field strength at 5 µm of B=800 fT. This amount is significantly greater than the 2.089 fT amount due to Brownian rotation.

A N48 neodymium magnet has a remnant induction of 1.38 Tesla. Using an algorithm provided by Arnold Magnetics for a cylindrical magnet 10 mm thick and 50 mm diameter at 1 mm above the surface center, the field strength is 0.250 T. For a cylindrical magnet 2 mm thick and 5 mm diameter at 1 mm above the surface center, the field strength is 0.274 T. The externally-applied magnetic field from the neodymium magnet will thus be about 250 to 270 mT, which is significantly greater than the 2.089 fT equivalent due to Brownian rotation.

The externally-applied magnetic field from a solenoid at a point $z_0$ (along its axis) is given by the equation (Reitz, J. et al. *Foundations of Electromagnetic* Theory, Third Edition, Addison-Wesley Publishing Co., 1980, pp. 171-72):

$$B_z(z_0) = (\mu_0 \cdot N \cdot I/L) \cdot \{(\cos[\arctan(a/(z_0+L/2))] + \cos[\arctan(a/(3L/2-z_0))])/2\}$$

where µ is 4π×10$^{-7}$ N·s$^2$·C$^{-2}$, N is the number of turns, I is the current, L is the length, and a is the radius.

Figure 19:
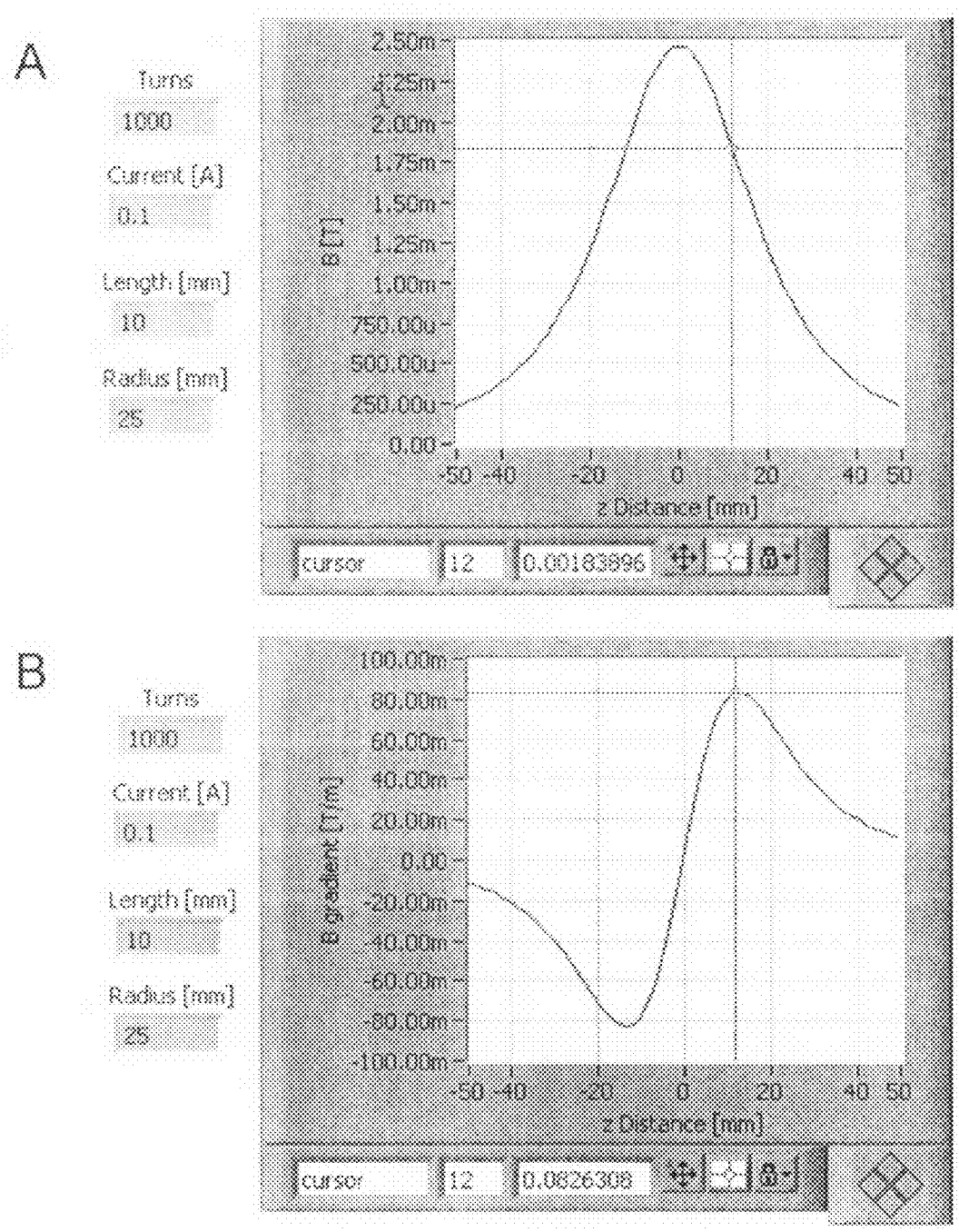
FIGS. 19A-19B show axial field strength and gradient for a typical solenoid.

Using the parameters N=1000, I=0.1 A, L=0.01 m, a=0.025 m, and $z_0$=0.012 m (7 mm past the end of the solenoid), the field structure can be graphed as in FIG. 19, which shows axial field strength and gradient for a solenoid.

The location of maximum gradient, not location of maximum field, is used to obtain the maximum linear force on a particle (vide infra). The field here is 1.839 mT, which is significantly greater than the 2.089 fT equivalent due to Brownian rotation.

Thus, a nearby neuron, a neodymium magnet, a solenoid, or other sources of magnetism, each produce sufficient field strengths to align magnetic particles despite the randomizing effect of Brownian rotation.

D. Maqnetic Particle Rotation Time Due to External Magnetic Field

A 500 nm particle core has a magnetic moment=1.043× 10$^{-14}$ A·m$^2$ (vide supra) and Torque (N·m)=magnetic dipole moment (A·m$^2$)×B magnetic field (N·A$^{-1}$·m$^{-1}$) (vide supra). Therefore, the torque applied by a solenoid to a particle is:

$$\text{Torque} = (1.043 \times 10^{-14} \text{ A·m}^2) \cdot (1.839 \times 10^{-3} \text{ N·A}^{-1}\cdot\text{m}^{-1}) = 1.918 \times 10^{-17} \text{ N·m}$$

To calculate the time to rotate based on viscosity, we first calculate the rotational friction coefficient:

$$f_r = 8 \cdot \pi n \cdot r^3 \text{ (the rotational equivalent of Stokes Law)}$$

where $f_r$ is the rotational friction coefficient, n is the dynamic viscosity, and r is the particle radius.

Using the following parameters:

$n$=4 cP=0.004 kg·m$^{-1}$·s$^{-1}$ for protoplasm (vide supra) and $r$=500×10$^{-9}$ m;

$f_r$=1.257×10$^{-20}$ kg·m$^2$·s$^{-1}$ and since Torque=$f_r \cdot v_r$ where $v_r$ is the angular velocity, $v_r$=(1.918×10$^{-17}$ kg·m$^2$·s$^{-2}$)/(1.257×10$^{-20}$ kg·m$^2$·s$^{-1}$)= 1526 rad·s$^{-1}$ For a 180°-rotation, the time would be approximately π/1526 rad·s$^{-1}$=2.059 ms This time would actually be slightly longer because of the added friction from the solvent shell around the particle and attached fluorescence detectable moiety being dragged with the particle as it rotates.

To calculate the time to rotate based on inertia, we first calculate the angular acceleration:

$$R = M/I$$

where R is the angular acceleration as rad·s$^{-2}$, M is the moment (torque)=1.918×10$^{-17}$ rad·kg·m$^2$·s$^{-2}$, and I is the moment of inertia=2.618×10$^{-28}$ kg·m$^2$. Therefore R=7.326× 10$^{+10}$ rad·s$^{-2}$.

For a 180° rotation, the time would be approximately

[π/7.326×10$^{+10}$ rad·s$^{-2}$]$^{1/2}$=6.548 µs

As above, time would actually be slightly longer because of the added moment of inertia from the solvent shell around the particle and attached fluorescence detectable moiety being dragged with the particle as it rotates.

Based on these exemplary calculations, it is apparent that rotational friction is the dominant factor determining how quickly a particle orients to an externally-applied magnetic field, since friction=2.059 ms and inertia=6.548 µs.

E. Magnetic Particle Rotation Delay Due to Surface Binding

Using the above rotational friction calculations, a 500× 10$^{-9}$ m radius non-bound particle has a rotation time of 2.059 ms. Assuming a receptor of length 10 nm, a bound particle is $510 \times 10^{-9}$ m radius, having $f_r = 1.334 \times 10^{-20}$ kg·m$^2$·s$^{-1}$ and $v_r = 1438$ rad·s$^{-1}$, which gives a rotation time of 2.185 ms.

To obtain a phase shift $\phi$ of 90° between the externally-applied magnetic field and the resultant particle rotation, the oscillation period would be $\pi/2 \cdot 2.059 \times 10^{-3}$ s = 3.234 ms, which corresponds to a frequency of $\gamma = 309.2$ Hz. At this frequency, the phase shift difference $\phi$ between non-bound and bound particles would be:

$$\gamma = [(2.185 \text{ ms} - 2.059 \text{ ms})/3.234 \text{ ms}] \cdot 360° = 14.0°$$

The ability to detect this phase shift difference $\phi$ is dependent on the effectiveness of occultation, fluorescence radiance, and the pixel noise of the detection photocell. The minimum detectable $\gamma$ will be determined empirically. The uniformity of the particle magnetic properties is critical to the detection resolution.

F. Magnetic Particle Migration Time Due to External Magnetic Field Gradient

To calculate the time for particle migration, we first calculate the translational friction coefficient:

$$f_t = 6 \cdot \pi \cdot n \cdot r \text{ (Stokes Law)}$$

where $f_t$ is the translational friction coefficient, n is the dynamic viscosity, and r is the particle radius.

Using the following parameters: n = 4 cP = 0.004 kg·m$^{-1}$·s$^{-1}$ for protoplasm (vide supra) and r = $500 \times 10^{-9}$ m; $f_t = 3.770 \times 10^{-8}$ kg·s$^{-1}$.

Since Force = $f_t \cdot v_t$, where $v_t$ is the translational velocity, the solenoid would give $$v_t = (8.657 \times 10^{-16} \text{ kg·m·s}^{-2})/(3.770 \times 10^{-8} \text{ kg·s}^{-1}) = 2.296 \times 10^{-8} \text{ m·s}^{-1}$$

For a 1 mm thick cuvette using the solenoid, the migration time would be approximately $$(0.001 \text{ m})/(2.296 \times 10^{-8} \text{ m·s}^{-1}) = 43554 \text{ s} = 12 \text{ hours}$$

Use of a 2 mm thick, 5 mm diameter neodymium magnet would exert a force of $1.523 \times 10^{-12}$ N (vide supra), resulting in a velocity of $4.040 \times 10^{-5}$ m·s$^{-1}$, giving a time span of 24.8 s, which is clearly more convenient.

Thus, while an arrangement using a solenoid for both rotating the particles and attracting them to the inner surface of a cuvette would be the easiest to engineer and implement, it may be advantageous to briefly use a neodymium magnet to perform the bulk of the particle migration. If a flat-bottomed well-plate were used as the cuvette, this would minimize mixing problems associated with convective currents. In some embodiments, a horizontal array of neodymium disk magnets is briefly used to pull particles down to the bottom inner surface, then removed and replaced with a solenoid to rotate them and maintain them at the bottom.

G. Occultation

The exemplary fluorescence detectable moiety emission wavelength is 490 nm (blue). These wavelengths are on the same size scale as the magnetic particle core and magnetic particle shell. As discussed above, if the magnetic particle-fluorescence detectable moiety compositions are aligned with an oscillating external magnetic field, the analytical signal will be the phase shift of the fluorescence intensity, resulting from the frictional and inertial drag on the pairs as they change alignment in response to the external field. Extending the measurement over many oscillations will improve the signal to noise ratio to help to obtain the phase shift distinctly, and thus a measure of the drag associated with surface binding.

The manner of fluorescence detectable moiety excitation may alleviate occultation problems. For example, if the excitation light is directed such that it reflects obliquely off of the inner surface of the cuvette, then the evanescent wave would extend into the sample media a sufficient distance to excite a forward-directed fluorescence detectable moiety, but not a sufficient distance for a back-directed fluorescence detectable moiety (Pouya, S. et al. *Experiments in Fluids* 2005, 39:784-86; Horak, D. et al. *Macromol. Mater. Eng.* 2004, 289:341-48), thereby minimizing background noise resulting from stray excitation light.

V. Detecting Changes in Fluorescence

A. Fluorescence Radiance

The measurement of fluorescence radiance (or "intensity") can be performed by a photocell fitted with a monochrome bandpass filter. The photocell signal is approximately linear with the intensity of the impinging photons, and is converted by the photocell electronics to an arbitrarily-scaled output voltage. Since only a narrow wavelength band will be used, and the lens/filter assembly will remain constant, the output voltage will be approximately linearly proportional to the fluorescent radiance.

Fluorescence radiance is dependent on three parameters: (i) the probability of absorbing a photon (molar extinction), (ii) the number of fluorophores, and (iii) the probability of radiative decay of the excited state (quantum yield) (Wang, L. et al. *J. Res. Nat'l Institute Standards Technology*, 2002.). The molar extinction coefficients of fluorescence detectable moiety are generally available. For example, the extinction coefficients of commercially available quantum dots is approximately $4 \times 10^5$ (at a molecular weight of 3 μg/mol), and the quantum yields are 30% to 50%. This provides a fluorescence radiance comparable to the best fluorescent dyes, explaining why quantum dots have been used in place of dyes in cellular microscopy (Gao, X. et al. *Current Opinion in Biotechnology* 2005, 16:63-72; Dubertret, B. et al. *Science* 2002, 298:1759-62; Winter, J. et al. *Adv. Mater.*, 2001, 13:1673-77; Crut, A. et al. *Nucleic Acids Res.*, 2005, 33:e98; Han, M. et al. *Nature, Biotechnology*, 2001, 19:631-35). In fact, the radiance is so strong that individual quantum dots can be imaged with conventional camera hardware and a 10 ms exposure time (Pouya, S. et al. *Experiments in Fluids* 2005, 39:784-86; Horak, D. et al. *Macromol. Mater. Eng.* 2004, 289:341-48).

B. Fluorescence Emission Detection

The optical detection of the fluorescence emission requires a sensor capable of measuring the emitted light at a frequency of 309.2 Hz, at a limited intensity. Photocells have better sensitivity and speed than CCD detectors; however, the use of CCDs would enable studying the behavior of individual quantum dots (Pouya, S. *Experiments in Fluids*, 2005, 39:784-86) and measuring how rotational rates are distributed across a population of magnetic particle-fluorescence detectable moiety compositions, such as might occur with partial occupancy of the available surface anti-ligands.

C. Altering the Behavior of Magnetic Particle Complexes

As noted above, particle rotation in a magnetic field is affected by the viscosity of the composition in which the particles are suspended or distributed. The present magnetic particles can be suspended in virtually any liquid or semi-solid medium that allows the particles to rotate or move in a magnetic field, does not interfere with excitation or fluorescence detection, and does not interfere with ligand-antiligand interactions. Water is a particularly non-viscous medium, while glycerol and gel matrices are examples of more viscous media. The behavior of the present magnetic particles can be modulated by increasing or decreasing the viscosity of the medium in which the magnetic particles are suspended.

D. Field Mapping

Since the magnetic field associated with a single cell is sufficient to cause rotation or movement of a magnetic particle (see, above), the present compositions are well suited for field-mapping, or in situ use. According to these embodiments, one of more of the above-described magnetic particles are introduced to a site in an animal (e.g., blood or other tissues), and then excited and monitored for fluorescence using appropriate optical equipment (i.e., adapted for use with a catheter or the like). In this manner, the binding of an analyte to the magnetic particles is determined at a local cite in an animal.

In further embodiments, fluorescent moiety-labeled magnetic particles are used to detect an electromagnetic event in the body, such as nerve "firing" (i.e., nerve cell depolarization and repolarization).

VI. Mixed Populations of Particles

Different populations of magnetic particles having different attached fluorescence detectable moieties can be combined in a single assay and distinguished based on emission color. This arrangement is particularly useful where the different populations of magnetic particles further have different ligand specificities.

Figure 21:
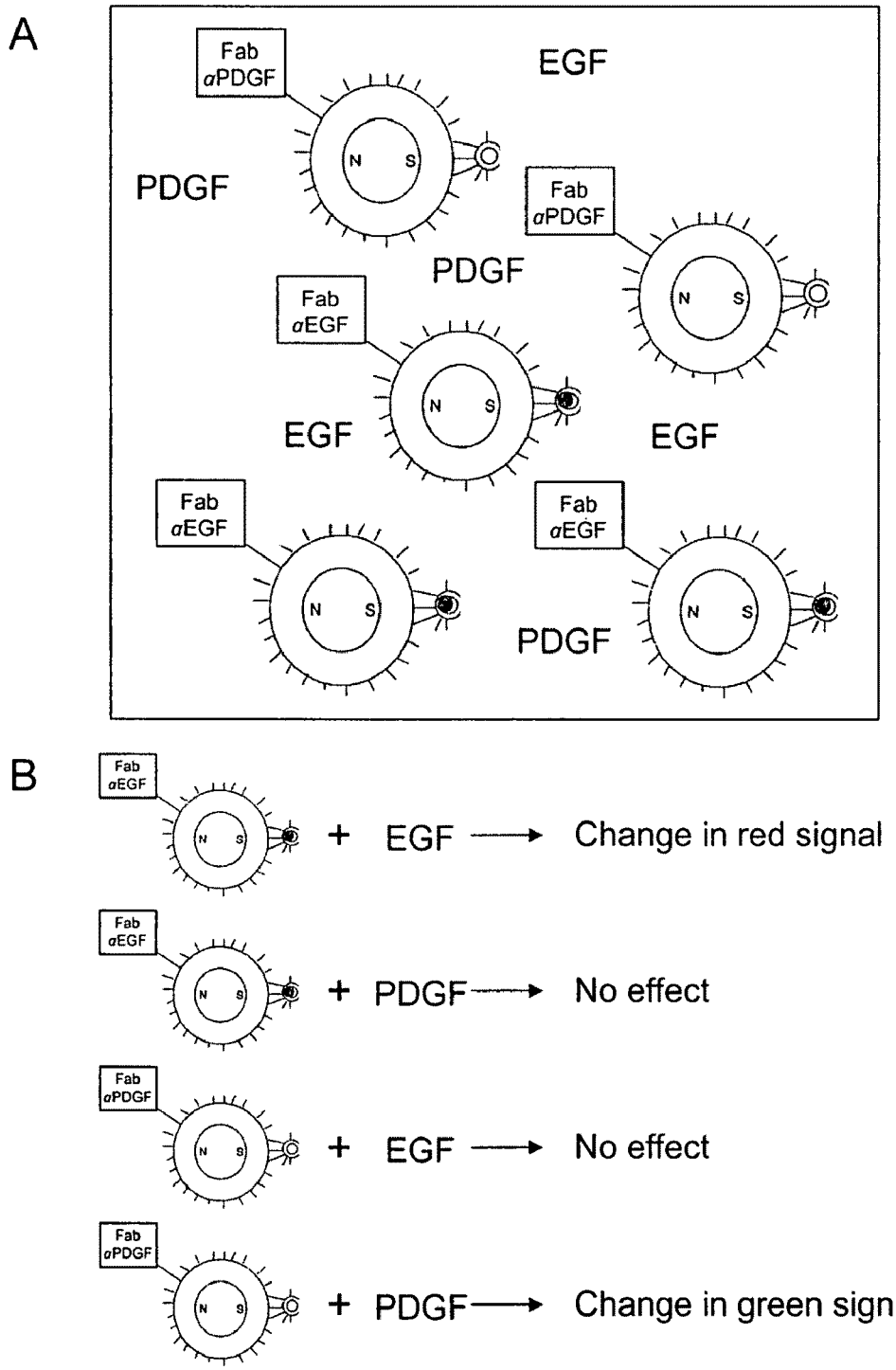
FIGS. 21A and 21B show an embodiment in which magnetic particles having different analyte specificities and different fluorescence detectable moieties are mixed and used to simultaneously detect a plurality of analytes.

FIG. 21 shows a mixture of two populations of particles. A first population includes red emission color quantum dots (grey cores) and anti-ligands (i.e., Fab antibody fragments) specific for epidermal growth factor (EGF). A second population of particles includes blue emission color quantum dots (white cores) and anti-ligands (i.e., Fab antibody fragments) specific for platelet-derived growth factor (PDGF). Note that other fluorescence detectable moieties can be used.

Because the ligand specificity of the magnetic particle compositions are different, and because the use of different emission color fluorescence detectable moieties (e.g., quantum dots) allows the independent detection of changes to the rotation/movement of the particles in a magnetic field upon attachment of the cognate ligand, EGF and PDGF can be independently measured in the same assay (FIG. 21A). As shown in FIG. 21B, only specific ligand-anti-ligand interactions affect the behavior of the magnetic particles, allowing a plurality of analytes to be separately detected in the same sample, using different emission color fluorescence detectable moiety-labeled magnetic particles appropriate specific anti-ligands.

VII. Analyte Characterization and Manipulation

Magnetic particles are readily collected using a magnet or a filter. Magnetic bead selection of cells, antibodies, and other biological molecules is well known. The skilled artisan will recognize that, in many cases, analytes attached to the magnetic particle can be collected, eluted, and further analyzed, and the particles recycled for further use.

In addition, the strength of analyte attachment to particles, i.e., via ligand-anti-ligand attached to the magnetic particles, can be further examined by increasing the rotation rate of the magnetic filed until the analyte is displaced by centripetal force or friction/drag with the solution, suspension, or semi-solid material in which the magnetic particles are analyzed. In this manner, the strength of antibody-antigen, receptor-ligand, nucleic acid, and other interactions can be measured. Additionally, the dynamic properties of the ligand-anti-ligand pair may be explored, such as the stretching that occurs during an increase in rotation rate, i.e., from the spingyness of a ligand-anti-ligand interaction.

VIII. Matrix or Screen Display Embodiments

As noted above, different emission-color fluorescence detectable moieties can be attached at different predetermined positions on a magnetic particle. A matrix of these particles can be distributed in a device capable of individually controlling the magnetic field of each particle, such that a different color emission is detectable from each particle from a given external fixed point, depending on the direction of the magnetic field applied to the particle. In this manner, fluorescence detectable moiety-labeled magnetic particle can be used as "pixels" in a matrix display screen. Individual "pixels" in different orientations are illustrated in FIGS. 22A-22C. The emission color observed from a given view angle (shows by the arrows) is indicated on the right side of the drawing.

FIG. 22D depicts a matrix display or screen comprising a population of magnetic particles having fluorescent moieties and distributed in a matrix. The matrix is adapted to apply a directional magnetic field to each particle, such that each particle (or pixel) appear "on" or "off", with respect to a particular color, depending on the direction of the magnetic field. Where each particle is attached to red, green, and blue fluorescent moieties (e.g., quantum dots) the matrix or screen can function in manner similar to a cathode ray tube or LCD monitor.

Although the invention has been described with respect to exemplary compositions and applications, if will be appreciated that various changes and modifications can be made without departing from the invention.

It is claimed:

1. A method of detecting the presence of an ligand analyte, comprising
    (a) exposing the analyte in solution to a fluorescence-detectable composition comprising (i) a magnetic particle having stable north and south-pole magnetic regions, (ii) one or more fluorescent moieties covalently linked to the magnetic particle and having an asymmetric spatial localization with respect to said north- and south-pole regions, and (iii) anti-ligand molecules covalently linked to the magnetic particle,
    (b) by said exposing binding the ligand analyte to the surface of said magnetic particle, thereby to increase the rotational drag of the composition when placed in an alternating or rotating electromagnetic field,
    (c) irradiating the composition with a fluorescence-excitation light beam, while rotating the composition in an alternating or rotating electromagnetic field, and
    (d) determining, from a measured phase lag of fluorescence emission from the composition, relative to the composition prior to ligand binding, the presence and/or amount of ligand bound to the analyte.

2. The method of claim 1, wherein the one or more fluorescent moieties include one or more quantum-dot particles, the sample and composition are placed in a transparent detection vessel, and which further includes placing the composition in a magnetic force effective to draw the composition adjacent a wall of the vessel, and said irradiating and measuring is carried out at said vessel wall.

3. The method of claim 1, wherein the one or more fluorescent moieties include one or more quantum-dot particles, and the vessel is a glass or quartz cuvette having a wall that supports total internal reflectance of the fluorescence excitation beam, wherein the composition is irradiated by evanescent fluorescence from the cuvette wall.

4. The method of claim 3, wherein said magnetic field and magnetic force are supplied by a solenoid supplied by an alternating electric current.

5. The method of claim 1, wherein the one or more fluorescent moieties include one or more quantum-dot particles suspended in micelles or a weak or dilute gelling agent, thus to minimize linear movement yet allow rotational movement during said irradiating and rotating step.

6. The method of claim 1, wherein the one or more fluorescent moieties include one or more quantum-dot particles, and said rotating step is carried out by (i) rotating the composition quickly to 90 degrees, and (ii) releasing the magnetic force on the composition momentarily, thus to cause identical poles to be opposed in a repellent orientation and thus force magnetic particles in the composition apart.

7. The method of claim 1, for use in detecting one or more of each of a plurality of analytes, the composition to which the analytes are exposed includes a plurality of compositions, each having a different fluorescence excitation wavelength, and said irradiating includes irradiating the compositions at different selected excitation wavelengths, to interrogate each of the compositions separately.

8. The method of claim 1, for use in measuring the binding affinity of a ligand analyte to an anti-ligand attached to such a composition, wherein said rotating step is carried out at a plurality of frequencies, to produce a plurality of composition rotational speeds, and the rotational speed effective to release the ligand from the composition is determined.

9. The method of claim 1, wherein the particles are placed in the rotating electromagnetic field prior to addition of the analyte.

10. A method of detecting the presence of an ligand analyte, comprising
(a) providing a fluorescence-detectable composition comprising (i) a magnetic particle having stable north and south-pole magnetic regions, (ii) one or more fluorescent moieties covalently linked to the magnetic particle and having an asymmetric spatial localization with respect to said north- and south-pole regions, and (iii) anti-ligand molecules covalently linked to the magnetic particle,
(b) placing said particles in an alternating or rotating electromagnetic field,
(c) irradiating the composition with a fluorescence-excitation light beam, while rotating the composition in an alternating or rotating electromagnetic field,
(d) exposing the ligand analyte to the surface of said magnetic particle to increase the rotational drag of the composition, and
(e) determining, from a measured phase lag of fluorescence emission from the composition, relative to the composition prior to ligand binding, the presence and/or amount of ligand bound to the analyte.

\* \* \* \* \*